United States Patent [19]

Mohrs et al.

[11] Patent Number: 5,006,534
[45] Date of Patent: Apr. 9, 1991

[54] SUBSTITUTED ETHERS, THIOETHERS AND AMINES FOR USE AS LIPOXYGENASE INHIBITORS

[75] Inventors: Klaus-Helmut Mohrs, Wuppertal; Romanis Fruchtmann, Cologne; Christian Kohlsdorfer, Erftstadt, all of Fed. Rep. of Germany

[73] Assignee: Bayer Aktiengesellschaft, Leverkusen, Fed. Rep. of Germany

[21] Appl. No.: 304,895

[22] Filed: Jan. 30, 1989

Related U.S. Application Data

[63] Continuation of Ser. No. 923,775, Oct. 27, 1986, abandoned.

[30] Foreign Application Priority Data

Nov. 16, 1985 [DE] Fed. Rep. of Germany ....... 3540743
May 22, 1986 [DE] Fed. Rep. of Germany ....... 3617183

[51] Int. Cl.$^5$ ................. A61K 31/47; A61K 31/425; C07D 215/24; C07D 21/702; C07D 277/64; C07D 277/76
[52] U.S. Cl. .................... 514/311; 514/307; 514/310; 514/312; 514/313; 514/367; 546/139; 546/147; 546/153; 546/155; 546/157; 546/159; 546/160; 546/171; 546/172; 546/178; 546/180; 548/152; 548/166; 548/178; 560/129; 568/631; 568/644; 568/658; 568/715
[58] Field of Search ............... 546/153, 155, 157, 159, 546/160, 171, 178, 180, 172; 514/311, 312, 313

[56] References Cited

U.S. PATENT DOCUMENTS

| | | | |
|---|---|---|---|
| 4,444,584 | 4/1984 | Serban et al. ....................... | 546/153 |
| 4,618,613 | 10/1986 | Hashizume et al. . | |
| 4,625,034 | 11/1986 | Neiss et al. ........................ | 546/155 |
| 4,631,287 | 12/1986 | Chakraborty et al. ............. | 546/178 |
| 4,661,499 | 4/1987 | Young et al. ....................... | 546/155 |
| 4,794,188 | 12/1988 | Musser et al. ....................... | 546/180 |

FOREIGN PATENT DOCUMENTS

| | | |
|---|---|---|
| 0079168 | 5/1983 | European Pat. Off. . |
| 0110405 | 6/1984 | European Pat. Off. . |
| 0113587 | 7/1984 | European Pat. Off. . |
| 0181568 | 5/1986 | European Pat. Off. . |
| 3337044 | 4/1985 | Fed. Rep. of Germany ...... 546/178 |
| 2253511 | 7/1975 | France . |

OTHER PUBLICATIONS

Grochowski et al., Chemical Abstracts, vol. 78, No. 3907x (1973).
Smith et al., Chemical Abstracts, vol. 68, No. 78579u (1968).
Derwent Abstract for German Patent 3337044 (4/25/85).
Bauer et al., Chemical Abstracts, vol. 96, 7068u (1982).

Primary Examiner—Mukund J. Shah
Assistant Examiner—E. Bernhardt
Attorney, Agent, or Firm—Sprung Horn Kramer & Woods

[57] ABSTRACT

Substituted benzyl ethers, benzyl thioethers, and benzylamines of the formula

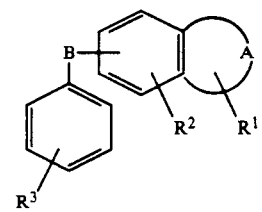

(I)

in which $R^1$ and $R^2$ are identical or different and represent hydrogen, alkyl, alkenyl, cycloalkyl, alkoxy, alkylthio, halogenoalkyl, sulphonylalkyl, halogenoalkoxy, halogenoalkylthio, aralkoxy, aralkylthio, halogen, nitro, cyano or hydroxyl, or represent a group of the formula

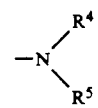

wherein
$R^4$ and $R^5$ are identical or different and represent hydrogen, alkyl, alkenyl, cycloalkyl, aralkyl, aryl or acyl,
$R^3$ represents a group of the formula

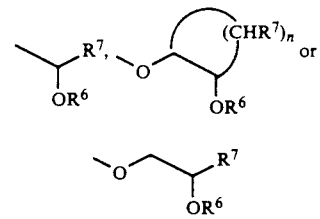

in which
$R^6$ represents hydrogen, alkyl or acyl,
$R^7$ represents hydrogen or alkyl and
n represents a number from 3 to 10,
B represents —CH$_2$—X— or —X—CH$_2$—,
wherein X represents O, S or NR$^7$,
and wherein $R^7$ has the abovementioned meaning and the group

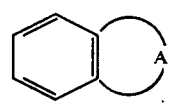

represents a benzo-fused heterocyclic system, A in the heterocyclic radical being 3-, 4- or 5-membered and containing nitrogen, oxygen and/or sulphur as heteroatoms. These compounds are lipoxygenase inhibitors.

6 Claims, No Drawings

SUBSTITUTED ETHERS, THIOETHERS AND AMINES FOR USE AS LIPOXYGENASE INHIBITORS

This application is a continuation of application Ser. No. 923,775, filed Oct. 27, 1986, now abandoned.

The invention relates to new substituted benzyl ethers, benzyl thioethers and benzylamines, processes for their preparation and their use in medicaments.

It is known from EP-OS (European Published Specification) No. 110,405 that benzyl 2-(1-hydroxyalkyl)-phenyl ethers and benzyl 3-(1-hydroxyalkyl)phenyl ethers have an antiallergic action.

The present invention relates to new substituted benzyl compounds of the general formula (I)

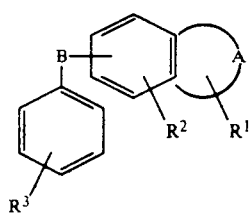

in which $R^1$ and $R^2$ are identical or different and represent hydrogen, alkyl, alkenyl, cycloalkyl, alkoxy, alkylthio, halogenoalkyl, sulphonylalkyl, halogenoalkoxy, halogenoalkylthio, aralkoxy, aralkylthio, halogen, nitro, cyano or hydroxyl, or represent a group of the formula

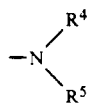

wherein $R^4$ and $R^5$ are identical or different and represent hydrogen, alkyl, alkenyl, cycloalkyl, aralkyl, aryl or acyl, $R^3$ represents a group of the formula

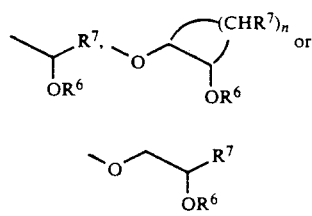

in which $R^6$ represents hydrogen, alkyl or acyl,
$R^7$ represents hydrogen or alkyl and
n represents a number from 3 to 10,
B represents —CH$_2$—X— or —X—CH$_2$—,
wherein X represents O, S or NR$^7$,
and wherein $R^7$ has the abovementioned meaning and the group

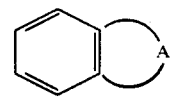

represents a benzo-fused heterocyclic system, A in the heterocyclic radical being 3-, 4- or 5-membered and containing nitrogen, oxygen and/or sulphur as heteroatoms.

In comparison with the known benzyl ethers, the substituted benzyl ethers according to the invention have, surprisingly, a higher pharmacological action.

Alkyl in general represents a straight-chain or branched hydrocarbon radical with 1 to 12 carbon atoms. Lower alkyl with 1 to about 8 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl in general represents a straight-chain or branched hydrocarbon radical with 2 to 12 carbon atoms and one or more, preferably with one or two, double bonds. The lower alkenyl radical with 2 to about 6 carbon atoms and one double bond is preferred. An alkenyl radical with 2 to 4 carbon atoms and one double bond is particularly preferred. Examples which may be mentioned are vinyl, allyl, propenyl, isopropenyl, butenyl, isobutenyl, pentenyl, isopentenyl, hexenyl, isohexenyl, heptenyl, isoheptenyl, octenyl and isooctenyl.

Cycloalkyl in general represents a cyclic hydrocarbon radical with 5 to 8 carbon atoms. The cyclopentyl and cyclohexyl radical are preferred. Examples which may be mentioned are cyclopentyl, cyclohexyl and cycloheptyl.

Alkoxy in general represents a straight-chain or branched hydrocarbon radical which has 1 to 12 carbon atoms and is bonded via an oxygen atom. Lower alkoxy with 1 to about 6 carbon atoms is preferred. An alkoxy radical with 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Alkylthio in general represents a straight-chain or branched hydrocarbon radical which has 1 to 12 carbon atoms and is bonded via a sulphur atom. Lower alkylthio with 1 to about 6 carbon atoms is preferred. An alkylthio radical with 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio and isooctylthio.

Halogenoalkyl in general represents straight-chain or branched lower alkyl with 1 to about 6 carbon atoms and one or more halogen atoms, preferably with one or more fluorine, chlorine and/or bromine atoms. Alkyl with 1 to 4 carbon atoms and with one or more fluorine and/or chlorine atoms is preferred. Alkyl with 1 or 2 carbon atoms and with up to five fluorine atoms or with up to three chlorine atoms is particularly preferred. Examples which may be mentioned are: fluoromethyl, chloromethyl, bromomethyl, fluoroethyl, chloroethyl, bromoethyl, fluoropropyl, chloropropyl, bromopropyl, fluorobutyl, chlorobutyl, bromobutyl, fluoroisopropyl, chloroisopropyl, bromoisopropyl, difluoromethyl, trifluoromethyl, dichloromethyl, trichloromethyl, difluoroethyl, dichloroethyl, trifluoroethyl, tetrafluoroethyl, pentafluoroethyl, trichloroethyl and trifluoropropyl. Trifluoromethyl, difluoromethyl, fluoromethyl, chloromethyl and trifluoroethyl are especially preferred.

Sulphonylalkyl in general represents a straight-chain or branched hydrocarbon radical which has 1 to 12 carbon atoms and is bonded via a sulphonyl group. Lower sulphonylalkyl with 1 to 6 carbon atoms is preferred. A sulphonylalkyl with 1 to 4 carbon atoms is particularly preferred.

Halogenoalkoxy in general represents a straight-chain or branched lower alkyl radical which has 1 to about 6 carbon atoms and one or more halogen atoms, preferably with one or more fluorine, chlorine and/or bromine atoms, and is bonded via an oxygen atom. Halogenoalkoxy with 1 to 4 carbon atoms and with one or more fluorine and/or chlorine atoms is preferred. Halogenoalkoxy with 1 or 2 carbon atoms and with up to 5 fluorine atoms or with up to 3 chlorine atoms is particularly preferred. Examples which may be mentioned are: fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, bromobutoxy, fluoroisopropoxy, chloroisopropoxy, bromoisopropoxy, difluoromethoxy, trifluoromethoxy, dichloromethoxy, trichloromethoxy, difluoroethoxy, trifluoroethoxy, tetrafluoroethoxy, pentafluoroethoxy, trichloroethoxy and trifluoropropoxy. Trifluoromethoxy, difluoromethoxy, fluoromethoxy, chloromethoxy and trifluoroethoxy are especially preferred.

Halogenoalkylthio in general represents a straight-chain or branched lower alkyl radical which has 1 to about 6 carbon atoms and one or more halogen atoms, preferably with one or more fluorine, chlorine and/or bromine atoms, and is bonded via a sulphur atom. Halogenoalkylthio with 1 to 4 carbon atoms and with one or more fluorine or chlorine atoms is preferred. Halogenoalkylthio with 1 or 2 carbon atoms and with up to five fluorine atoms or with up to 3 chlorine atoms is particularly preferred. Examples which may be mentioned are: fluoromethylthio, chloromethylthio, bromomethylthio, fluoroethylthio, chloroethylthio, bromoethylthio, fluoropropylthio, chloropropylthio, bromopropylthio, fluorobutylthio, bromobutylthio, chlorobutylthio, fluoroisopropylthio, chloroisopropylthio, bromoisopropylthio, difluoromethylthio, trifluoromethylthio, dichloromethylthio, trichloromethylthio, difluorethylthio, trifluoroethylthio, tetrafluoroethylthio, pentafluoroethylthio, trichloroethylthio, trifluoropropylthio, pentafluoroethylthio, trichloroethylthio and trifluoropropylthio. Trifluoromethylthio, difluoromethylthio, fluoromethylthio, chloromethylthio and trifluoroethylthio are especially preferred.

Aryl in general represents an aromatic radical with 6 to about 12 carbon atoms. Preferred aryl radicals are phenyl, naphthyl and bisphenyl.

Aralkyl in general represents an aryl radical which has 7 to 14 carbon atoms and is bonded via an alkylene chain. Aralkyl radicals with 1 to 6 carbon atoms in the aliphatic part and 6 to 12 carbon atoms in the aromatic part are preferred. The following aralkyl radicals may be mentioned as examples: benzyl, naphthylmethyl, phenethyl and phenylpropyl.

Aralkoxy in general represents an aralkyl radical with 7 to 14 carbon atoms, the alkylene chain being bonded via an oxygen atom. Aralkoxy radicals with 1 to 6 carbon atoms in the aliphatic part and 6 to 12 carbon atoms in the aromatic part are preferred. The following aralkoxy radicals may be mentioned as examples: benzyloxy, naphthylmethoxy, phenethoxy and phenylpropoxy.

Aralkylthio in general represents an aralkyl radical with 7 to 14 carbon atoms, the alkyl chain being bonded via a sulphur atom. Aralkylthio radicals with 1 to 6 carbon atoms in the aliphatic part and 6 to 12 carbon atoms in the aromatic part are preferred. The following aralkylthio radicals may be mentioned as examples: benzylthio, naphthylmethylthio, phenethylthio and phenylpropylthio.

Acyl in general represents phenyl or straight-chain or branched lower alkyl with 1 to about 6 carbon atoms, which are bonded via a carbonyl group. Phenyl and alkyl radicals with up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Halogen in general represents fluorine, chlorine, bromine or iodine, preferably fluorine, chlorine or bromine. Halogen particularly preferably represents fluorine or chlorine.

The benzo-fused heterocyclic system in general represents a phenyl radical onto which a 5- to 7-membered heterocyclic radical with 1 to 3 nitrogen, sulphur and/or oxygen atoms is fused. 5- to 6-membered heterocyclic systems with 1 or 2 nitrogen, oxygen and/or sulphur atoms are preferred. Examples which may be mentioned are: quinoline, isoquinoline, cinnoline, quinazoline, quinoxaline, phthalazine, quinoline N-oxide, isoquinoline N-oxide, quinazoline N-oxide, quinoxalinone, quinoxalinedione, phthalazinedione, chroman, chromene, chromone, thiochroman, thiochromene, thiochromone, indole, indolone, isatine, isoindole, isoindolone, benzofuran, benzothiophene, benzimidazole, benzimidazolone, benzoxazole, benzothiazole, benzisoxazole, benzisothiazole, benzothiadiazole, benzoxadiazole, indazole and indoxyl.

Preferred compounds of the general formula (I) are those
in which $R^1$ and $R^2$ are identical or different and represent hydrogen, lower alkyl, lower alkenyl, cyclopentyl, cyclohexyl, lower alkoxy, lower alkylthio, halogeno-lower alkyl, sulphonyl-lower alkyl, halogeno-lower alkoxy, halogeno lower alkylthio, benzyloxy, benzylthio, fluorine, chlorine, bromine, nitro, cyano or hydroxyl, or represent a group of the formula

wherein
$R^4$ and $R^5$ are identical or different and represent hydrogen, lower alkyl, lower alkenyl, cyclopentyl, cyclohexyl, benzyl, phenyl, benzoyl or acetyl,
$R^3$ represents a group of the formula

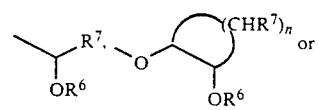

-continued $$\diagdown O \diagdown \begin{matrix} R^7 \\ | \\ OR^6 \end{matrix}$$

wherein
R⁶ represents, hydrogen, lower alkyl, benzoyl or lower alkanoyl,
R⁷ represents hydrogen or lower alkyl and
n represents a number from 3 to 8,
B represents —CH₂—X—,
wherein X represents O, S or NR⁷,
and wherein R⁷ has the abovementioned meaning, and the group

[bicyclic ring structure labeled A]

represents quinoline, isoquinoline, cinnoline, quinoline N-oxide, quinazoline, isoquinoline N-oxide, quinoxaline, phthalazine, quinolone, isoquinolone, cinnolinone, quinazolinedione, quinoxazolinone, quinoxalinedione, phthalazinedione, indole, indolone, isoindole, isoindolone, benzofuran, benzothiophene, benzimidazole, benzoxazole, benzothiazole, indazole or indoxyl.

Particularly preferred compounds of the general formula (I) are those
in which R¹ and R² are identical or different and represent hydrogen, methyl, ethyl, propyl, isopropyl, allyl, methoxy, ethoxy, methylthio, ethylthio, trifluoromethoxy, trifluoromethylthio, fluorine, chlorine, bromine, nitro, cyano, ethylsulphonyl or hydroxyl, or represent a group of the formula $$-N \diagup \begin{matrix} R^4 \\ \\ R^5 \end{matrix}$$

wherein
R⁴ and R⁵ are identical or different and represent hydrogen, methyl, ethyl, propyl, isopropyl, allyl, benzyl, phenyl or acetyl,
R³ represents a radical of the formula

[structures showing R⁷, OR⁶, (CHR⁷)ₙ, OR⁶] or $$\diagdown O \diagdown \begin{matrix} R^7 \\ | \\ OR^6 \end{matrix}$$

wherein
R⁶ represents hydrogen, methoxy, benzoyl, acetyl, ethylcarbonyl or propylcarbonyl,
R⁷ represents hydrogen, or represents a straight or branched alkyl chain with up to 8C atoms and
n represents a number from 3 to 4,
B represents —CH₂—X—,
wherein X represents O, S or NR⁷,
and wherein R⁷ has the meaning given, and the group of the formula

[bicyclic ring structure labeled A]

represents quinoline, quinoline N-oxide, isoquinoline, isoquinoline N-oxide, cinnoline, quinazoline, quinoxaline, phthalazine, quinolone, isoquinolone, indole, indolone, isoindole, benzofuran, benzothiophene, benzimidazole, benzothiazole, benzoxazole or indazole.

The following active compounds may be mentioned specifically as examples: 1-[3-(quinolin-8-yloxymethyl)-phenyl]pentyl acetate, 1-[3-(quinolin-8-yloxymethyl)-phenyl]heptyl acetate, 1-[3-(quinolin-8-yloxymethyl)-phenyl]heptyl acetate, 1-[3-(5,7-dichloroquinolin-8-yloxymethyl)phenyl]-heptyl acetate, 1-[2-(5,7-dichloroquinolin-8-yloxymethyl)phenyl]pentyl acetate, 2-[3-(quinolin-8-yloxymethyl)phenoxy]cyclohexyl acetate, 1-[2-(2-(1H)-quinolon-8-yloxymethyl)phenoxymethyl]propyl acetate, 2-[3-(2-(1H)-quinolon-8-yloxymethyl)phenoxy]cyclohexyl acetate (trans form), 1-[3-(2-(1H)-quinolon-8-yloxymethyl)phenyl]hexyl acetate, 1-[3-(2-(1H)-quinolon-8-yloxymethyl)phenyl]heptyl acetate, 1-[3-(2-(1H)-quinolon-8-yloxymethyl)phenoxymethyl]propyl acetate, 1-[2-(2-(1H)-quinolon-8-yloxymethyl)phenyl]hexyl acetate, 1-[2-(2-quinolin-8-yloxymethyl)phenyl]heptyl acetate, 1-[2-(quinoline N-oxide 8-yloxymethyl)phenyl]hexyl acetate, 1-[3-(quinolin-8-yloxymethyl)phenyl]hexyl acetate, 1-[4-(quinolin-8-yloxymethyl)phenyl]pentyl acetate, 1-[3-(isoquinolin-5-yloxymethyl)phenyl]pentyl acetate, 1-[3-(quinolin-8-ylaminomethyl)phenyl]pentyl acetate, 1-[3-(quinolin-8-ylthiomethyl)phenyl]pentyl acetate, 1-[3-(quinolin-8-yloxymethyl)phenoxymethyl]pentyl acetate, 1-[3-(quinolin-8-yloxymethyl)phenoxymethyl]propyl acetate, 1-[2-(quinolin-8-yloxymethyl)phenoxymethyl]propyl acetate, 1-[3-(quinolin-8-yloxymethyl)phenoxymethyl] 2,2-dimethyl-propyl acetate, 1-[3-(5,7-dichloroquinolin-8-yloxymethyl)phenyl]pentyl acetate, 1-[3-(quinolin-8-yloxymethyl)phenoxymethyl]-2,2-dimethyl-propanol, 1-[3-(quinolin-8-yloxymethyl)-phenoxymethyl]pentanol, 1-[3-(isoquinolin-5-yloxymethyl)phenyl]pentanol, 1-[3-(quinolin-8-ylaminomethyl)phenyl]pentanol, 1-[3-(2-methylquinolin-8-yloxymethyl)phenyl]hexanol, 1-[2-(1-oxoquinolin-8-yloxymethyl)phenyl]hexanol, 1-[2-(quinolin-8-yloxymethyl)phenoxymethyl]propanol, 1-[3-(quinolin-8-yloxymethyl)phenoxymethyl]propanol, 1-[3-(quinolin-8-ylthiomethyl)phenyl]pentanol, 1-[3-(quinolin-8-yloxymethyl)phenyl]heptanol, 1-[3-(quinolin-8-yloxymethyl)phenyl]hexanol, 1-[3-(2-quinolin-8-yloxymethyl)phenyl]heptanol, 1-[3-(2-quinolin-8-yloxymethyl)phenyl]hexanol, 2-[3-(2-(1H)-quinolon-8-yloxymethyl)phenoxy]cyclohexanol (transform), 1-[2-(quinolin-8-yloxymethyl)phenyl]pentanol, 1-[3-(5,7-dichloroquinolin-8-yloxymethyl)-phenyl]heptanol, 1-[3-(2-(1H)-quinolon-8-yloxymethyl)phenoxymethyl]propanol, 1-[2-(quinolin-8-yloxymethyl)phenyl]hexanol, 1-[3-(quinolin-8-yloxymethyl)phenyl]pentanol, 1-[2-(2-(1H)-quinolon-8-yloxymethyl)phenyl]hexanol, 1-[2-(2-(1H)-quinolon-8-yloxymethyl)phenoxymethyl]propanol and 1-[2-(2-(1H)-quinolon-8-yloxymethyl)phenyl]heptanol, 1-[3-(quinolin-8-yloxymethyl)phenyl]-3-methylbutyl acetate, 1-[3-(quinolin-8-yloxymethyl)phenyl]-hexyl propionate, 1-[3-(4-methylquinolin-8-yloxymethyl)-phenyl]-pentyl acetate, 1-[3-(4-chloroquinolin-8-yloxymethyl)phenyl]-pentyl acetate, 1-[3-(6-methylquinolin-8-yloxymethyl)phenyl]-pentyl acetate, 1-[3-(6-nitroquinolin-8-yloxymethyl)phenyl]-pentyl acetate, 1-[3-(2-ethylsulphonylbenzothiazol-7-yl-aminomethyl)phenyl]hexyl acetate, 1-[4-(quinolin-8-xyloxymethyl)phenyl]pentanol, 1-[3-(quinolin-8-yloxymethyl)phenyl]-3-methylbutanol, 1-[3-(2-ethylsulphonylbenzothiazol-7-yloxymethyl)phenyl]hexanol, 1-[3-(4-chloroquinolin-8-yloxymethyl)phenyl]pentanol, 1-[3-(4-methylquinolin-8-yloxymethyl)phenyl]pentanol, 1-[3-(6-methylquinolin-8-yloxymethyl)phenyl]pentanol, 8-[3-(1-methoxypentyl)benzyl]oxyquinoline and 1-[3-(quinolin-8-yloxymethyl)pehnyl]pentyl benzoate.

A process has furthermore been found for the preparation of substituted benzyl ethers of the formula

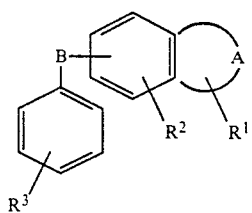
(I)

in which $R^1$ and $R^2$ are identical or different and represent hydrogen, alkyl, alkenyl, cycloalkyl, alkoxy, alkylthio, halogenoalkyl, sulphonylalkyl, halogenoalkoxy, halogenoalkylthio, aralkoxy, aralkylthio, halogen, nitro, cyano or hydroxyl, or represent a group of the formula

wherein $R^4$ and $R^5$ are identical or different and represent hydrogen, alkyl, alkenyl, cycloalkyl, aralkyl, aryl or acyl, $R^3$ represents a group of the formula

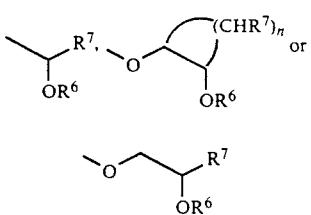

in which $R^6$ represents hydrogen or acyl, $R^7$ represents hydrogen or alkyl and n represents a number from 3 to 10, B represents —CH$_2$—X— or —X—CH$_2$—, wherein X represents O, S or NR$^7$, and wherein $R^7$ has the abovementioned meaning and the group

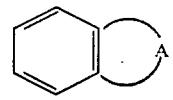

represents a benzo-fused heterocyclic system, A in the heterocyclic radical being 3-, 4- or 5-membered and containing nitrogen, oxygen and/or sulphur as heteroatoms, characterized in that (a) in the preparation of benzyl ethers where B is —CH$_2$—X—, halides of the general formula (II)

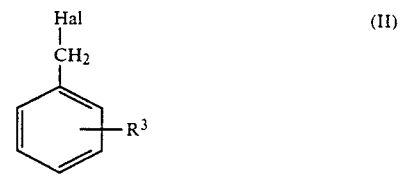
(II)

in which $R^3$ represents a group of the formula

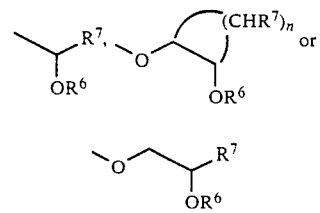

wherein $R^6$ represents acyl, $R^7$ represents hydrogen or alkyl and n represents a number from 3 to 10, and Hal represents chlorine, bromine or iodine, are reacted with compounds of the general formula (III)

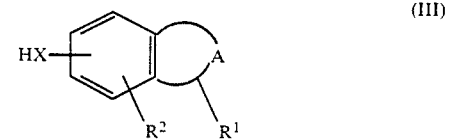
(III)

in which $R^1$ and $R^2$ are identical or different and represent hydrogen, alkyl, alkenyl, cycloalkyl, alkoxy, alkylthio, halogenoalkyl, sulphonylalkyl, halogenoalkoxy, halogenoalkylthio, aralkoxy, aralkylthio, halogen, nitro, cyano or hydroxyl, or represent a group of the formula

wherein $R^4$ and $R^5$ are identical or different and represent hydrogen, alkyl, alkenyl, cycloalkyl, aralkyl, aryl or acyl and X represents O, S or NR$^7$, wherein R⁷ has the abovementioned meaning, and the group

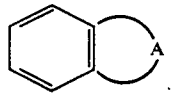

represents a benzo-fused heterocyclic system, A in the heterocyclic radical being 3-, 4- or 5-membered and containing nitrogen, oxygen and/or sulphur as heteroatoms, or (b) in the preparation of benzyl ethers where B is —X—CH$_2$—, halogen compounds of the formula IV

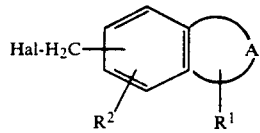

(IV)

in which $R^1$ and $R^2$ are identical or different and represent hydrogen, alkyl, alkenyl, cycloalkyl, alkoxy, alkylthio, halogenoalkyl, sulphonylalkyl halogenoalkoxy, halogenoalkylthio, aralkoxy, aralkylthio, halogen, nitro, cyano or hydroxyl, or represent a group of the formula

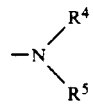

wherein
  $R^4$ and $R^5$ are identical or different and represent hydrogen, alkyl, alkenyl, cycloalkyl, aralkyl, aryl or acyl and
  X represents O, S or NR⁷,
wherein R⁷ has the abovementioned meaning, and the group

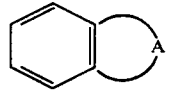

represents a benzo-fused heterocyclic system, in the heterocyclic radical being 3-, 4- or 5-membered and containing nitrogen, oxygen and/or sulphur as heteroatoms, and Hal represents chlorine, bromine or iodine, are reacted with compounds of the general formula V

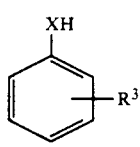

(V)

in which R³ represents a group of the formula

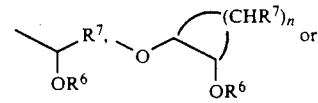

or

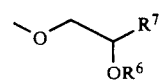

wherein
  R⁶ represents acyl,
  R⁷ represents hydrogen or alkyl and
  n represents a number from 3 to 10, and
  X represents O, S or NR⁷,
wherein R⁷ has the abovementioned meaning, in inert organic solvents, if appropriate in the presence of a base, and, if appropriate, the acyl groups present are split off.

The process according to the invention can be illustrated, for example, by the following equation:

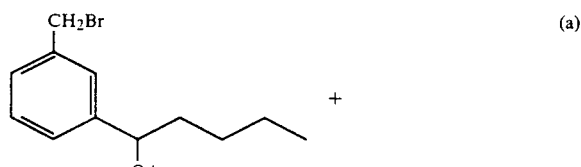

(a)

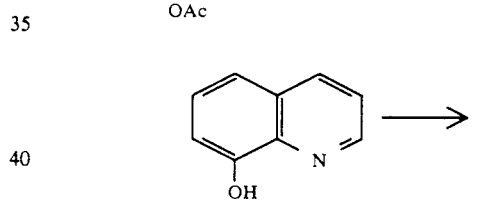

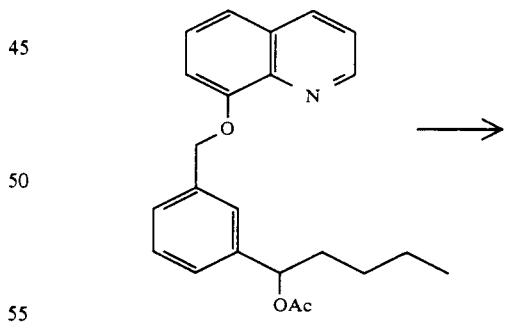

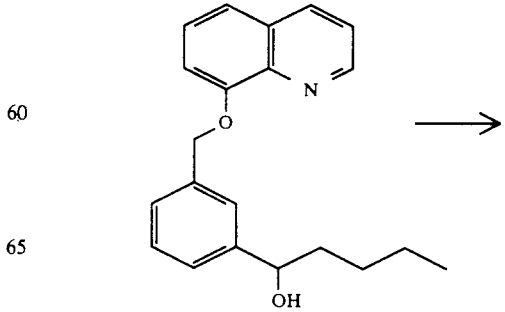

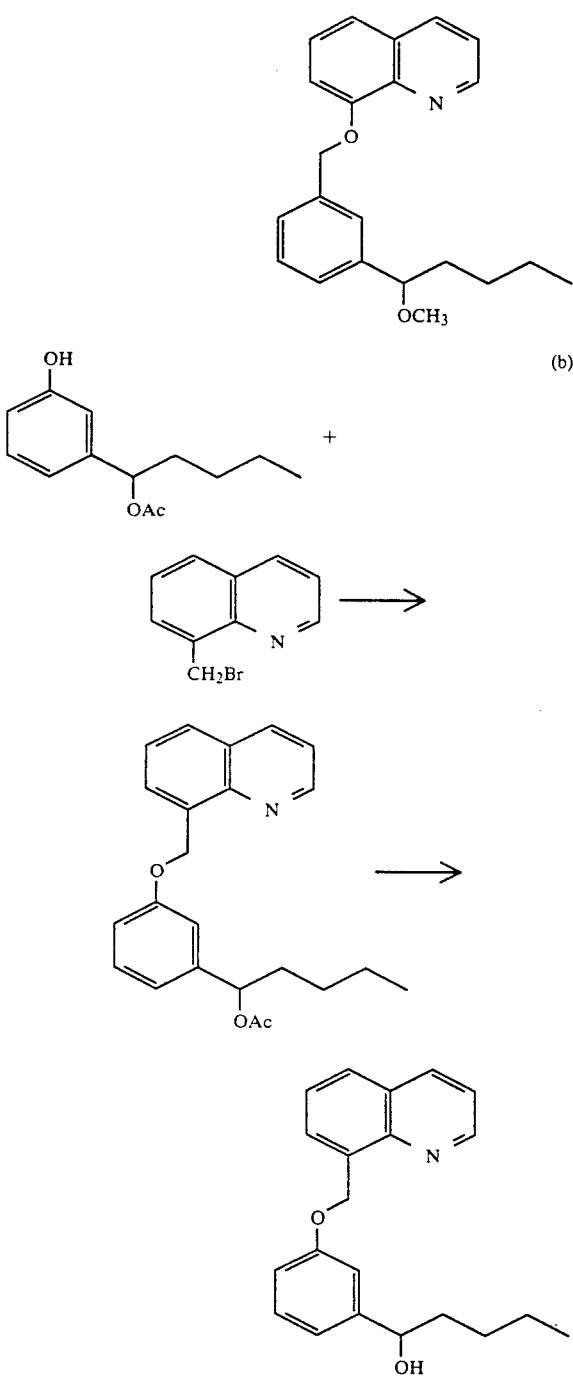

Solvents for the process according to the invention can be inert organic solvents which are not changed under the reaction conditions. These include, preferably, alcohols, such as, for example, methanol, ethanol, propanol or isopropanol, ethers, such as, for example, dioxane, tetrahydrofuran or diethyl ether, halogenohydrocarbons, such as methylene chloride, chloroform, carbon tetrachloride, 1,2-dichloroethane or trichloroethylene, hydrocarbons, such as benzene, xylene, toluene, hexane, cyclohexane or petroleum fractions, nitromethane, dimethylformamide, acetonitrile, acetone or hexamethylphosphoric acid triamide. It is likewise possible to use mixtures of the solvents.

Inorganic or organic bases can be used as bases for the process according to the invention. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or organic amines (trialkyl($C_1$-$C_6$)amines), such as triethylamine, and heterocyclic compounds, such as pyridine, methylpiperidine, piperidine or morpholine.

It is also possible to use alkali metals, such as sodium, and hydrides thereof, such as sodium hydride, as bases.

The compounds according to the invention are in general prepared in a temperature range from 0° C. to 150° C., preferably from 10° C. to 100° C.

The process according to the invention is in general carried out under normal pressure. However, it is also possible to carry out the process under reduced pressure or increased pressure (for example in a range from 0.5 to 5 bar).

In general, 0.5 to 5, preferably 1 to 2, mol of halide are employed per mol of the reaction partner. The base is in general used in an amount of 0.5 to 5 mol, preferably 1 to 3 mol, based on the halide.

The acyl group can be split off, for example, by addition of bases. Examples of bases which may be mentioned are sodium hydroxide, potassium hydroxide, barium hydroxide, sodium carbonate or potassium carbonate.

In general 1 to 5 mol, preferably 2 to 4 mol, of the base are employed per mol of acyl compound.

The alkylation of the hydroxy compounds (formula I with $R^6$=H) is carried out in general in inert solvents, if appropriate in the presence of a base, with customary alkylating agents, such as alkyl halides, for example $C_1$-$C_4$-alkyl chlorides, bromides or iodides, dialkyl sulphates, for example dimethyl sulphate, or diazoalkanes, for example diazomethane, diazoethane or diazopropane.

Depending on the type of alkylating agent, suitable solvents for this purpose are all inert organic solvents. These preferably include ethers, such as diethyl ether, dioxane or tetrahydrofuran, or hydrocarbons, such as benzene, toluene or xylene, or dimethylformamide or hexamethylphosphoric acid triamide, or mixtures of the stated solvents.

Suitable bases are the customary basic compounds. These preferably include alkali metal hydrides, such as sodium hydride, alkali metal amides, such as sodium amide or lithium diisopropylamide, alkali metal alcoholates, such as sodium methylate, sodium ethylate, potassium methylate, potassium ethylate or potassium tert-butylate, or organic amines such as trialkylamines, for example triethylamine, or organolithium compounds, such as butyllithium or phenyllithium.

The process according to the invention can be carried out, for example, as follows:

The OH, SH or NH-acid starting compound, a diluent and, if appropriate, a base are mixed and the halide is added, if appropriate in a diluent. If appropriate, the mixture can be warmed. Working up is carried out in a manner which is known per se.

The starting compounds of the general formula (III) are known or can be prepared by known methods (A. R. Katritzky, C. W. Reeds, Comprehensive Heterocyclic Chemistry Volume 1-8, Pergamon Press).

The starting compounds of the general formula IV are known or can be prepared by known methods (EP-OS (European Published Specification) No. 13,411). The starting compounds of the general formula V are known or can be prepared by known methods (EP-OS (European Published Specification) No. 110,405).

The benzyl halides of the formula (II) used as starting compounds are new. They can be prepared by a process in which tolyl compounds of the general formula (VI)

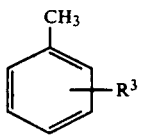
(VI)

in which R³ represents a group of the formula

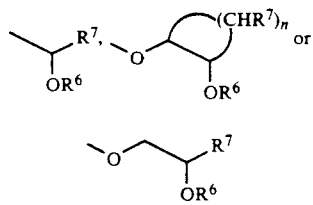

wherein
R⁶ represents acyl,
R⁷ represents hydrogen or alkyl and
n denotes a number from 3 to 10,
are reacted with halogenating agents in suitable solvents, if appropriate in the presence of agents which form free radicals.

The reaction can be illustrated by the following equation:

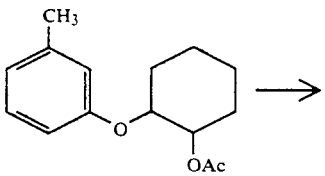

Suitable solvents are all the inert organic solvents which do not change under the reaction conditions.

These include, preferably, halogenohydrocarbons, such as, for example, methylene chloride, chloroform or carbon tetrachloride, hydrocarbons, such as benzene, toluene or xylene, or glacial acetic acid.

The generally customary halogenating agents can be used as the halogenating agents. Chlorine, bromine, N-chlorosuccinimide (NCS) or N-bromosuccinimide (NBS), if appropriate in the presence of agents which form free radicals, such as azobisisobutyronitrile (AIBN), benzoyl peroxide or light, are preferred. Bromination with NBS and AIBN in carbon tetrachloride is particularly preferred.

The reaction temperatures can in general be varied within a wide range. The reaction is preferably carried out in a range from $-10°$ C. to $100°$ C., particularly preferably from $0°$ C. to $80°$ C.

The reaction can be carried out under normal pressure, but also under increased or reduced pressure. It is in general carried out under normal pressure.

The proportion of the reactants can in general be chosen as desired. However, the reaction is preferably carried out with an amount of 1 to 5 mol, particularly preferably 1 mol, of the halogenating agent per mol of the tolyl compound.

The tolyl compounds used as the starting compound are known or can be prepared by known methods in accordance with the following general equation:

a. for R³ = 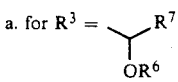

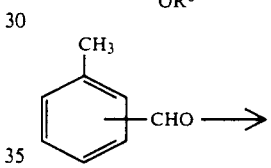

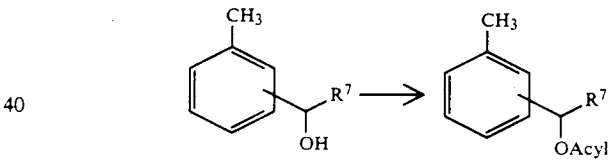

According to this equation, the corresponding tolylaldehydes (VII) are reacted with organometallic compounds, preferably organolithium compounds or Grignard reagents, by known methods to give the corresponding alcohols, which are then acylated on the hydroxyl group by customary methods. The processes are described, for example, by U. Schollkopf in Houben-Weyls "Methoden der organischen Chemie" ("Methods of Organic Chemistry") XIII/1, page 175 et seq.; by K. Nutzel in Houben-Weyls "Methoden der organischen Chemie" ("Methods of Organic Chemistry") XIII/2a, page 285 et seq.; and by E. Schumann in Houben-Weyls "Methoden der organischen Chemie" ("Methods of Organic Chemistry") VI/1b, page 823 et seq.

b. for R³ = 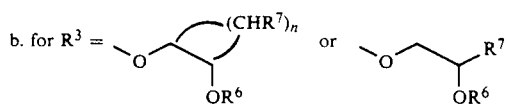

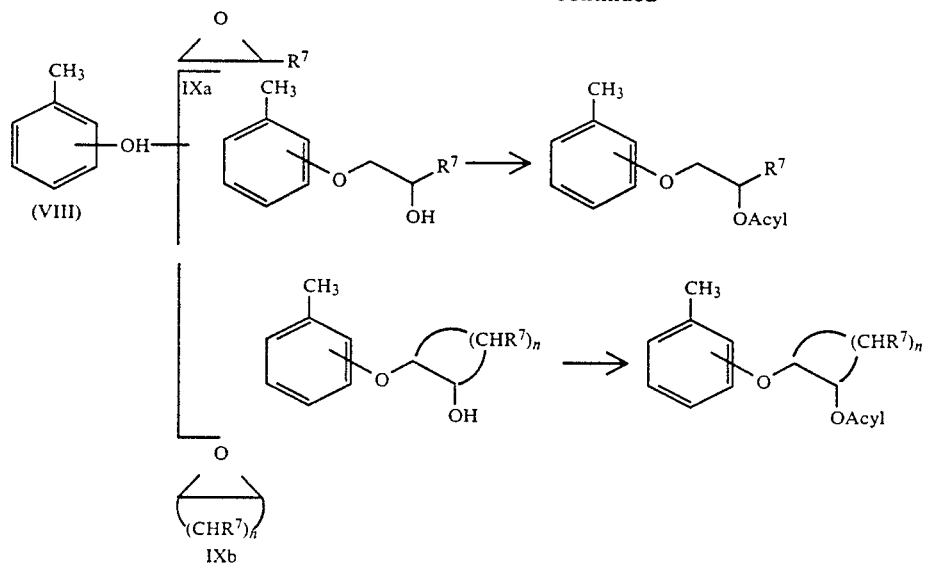

According to this equation, the corresponding cresols (VIII) are reacted with epoxides IXa, by known methods to give the corresponding hydroxy-ethers and the hydroxyl group is then acylated by known methods. These processes are described, for example, by G. Dittus in Houben-Weyls "Methoden der organischen Chemie" ("Methods of Organic Chemistry") VI/3, page 456 et seq., and by E. Schaumann in Houben-Weyls "Methoden der organischen Chemie" ("Methods of Organic Chemistry") VI/1b, page 823 et seq.

The tolylaldehydes and cresols used as starting substances are known: Beilstein's Handbuch der organischen Chemie (Beilstein's Handbook of Organic Chemistry), 7, 295–297, and 6, 349, 373 and 389.

The benzyl compounds according to the invention can be employed as active compounds in medicaments. The substances act as inhibitors of enzymatic reactions in the context of arachidonic acid metabolism, in particular of lipoxygenase.

They are thus preferably suitable for the treatment and prevention of diseases of the respiratory tract, such as allergies/asthma, bronchitis, emphysemas, shock lung, pulmonary hypertension, inflammations/rheumatism and oedemas, thromboses and thrombo-embolisms, ischaemias (disturbances in peripheral, cardiac or cerebral circulation), cardiac and cerebral infarctions, disorders in cardiac rhythm, angina pectoris and arterial sclerosis, for tissue transplants, dermatoses, such as psoriasis, and metastases, and for cytoprotection in the gastrointestinal tract.

The new active compounds can be converted in a manner which is known per se into the customary formulations, such as tablets, capsules, dragees, pills, granules, aerosols, syrups, emulsions, suspensions and solutions, using inert non-toxic, pharmaceutically suitable excipients or solvents. The therapeutically active compound should in each case be present here in the total mixture in a concentration of about 0.5 to 90% by weight, preferably 10 to 70% by weight, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case of the use of water as a diluent, organic solvents can be used, if appropriate, as auxiliary solvents.

Examples of auxiliaries which may be mentioned are: water, non-toxic organic solvents, such as paraffins (for example petroleum fractions), vegetable oils (for example groundnut/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders, (for example highly disperse silicic acid and silicates) and sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration can be effected in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various adjuvants, such as starch, preferably potato starch, gelatine and the like. Lubricants, such as magnesium stearate, sodium lauryl-sulphate and talc, can furthermore be co-used for tablet-making. In the case of aqueous suspensions and/or elixirs intended for oral use, various flavour correctants or dyestuffs can be added to the active compounds, in addition to the abovementioned auxiliaries.

In the case of parenteral use, solutions of the active compounds can be employed, using suitable liquid excipients.

In general, it has proved advantageous in the case of intravenous administration to administer amounts of about 0.001 to 1 mg/kg, preferably about 0.01 to 0.5 mg/kg of body weight to achieve effective results. In the case of oral administration, the dosage is in general about 0.01 to 20 mg/kg, preferably 0.1 to 10 mg/kg of body weight.

Nevertheless, it may be necessary, if appropriate, to deviate from the amounts mentioned, and in particular as a function of the body weight or of the nature of the administration route, of the individual behaviour towards the medicament, of the nature of its formulation and at the time or interval at which administration takes place. Thus it can in some cases suffice to manage with less than the abovementioned minimum amount, whilst in other cases the upper limit mentioned must be exceeded. Where relatively large amounts are administered, it may be advisable to distribute these into several individual doses over the day.

The substituted benzyl ethers according to the invention can be used both in human medicine and in veterinary medicine.

PREPARATION EXAMPLES

The retention times $R_f$(min) are determined using an HPLC apparatus (Knauer) on Hibar columns (Merck).
System a: RP-8.5 μm, Throughput: 1.5 ml/min, Eluant:Acetonitrile/water=70:30 (v/v)
System b: RP-8.7 μm, Throughput: 2.0 ml/min, Eluant:Acetonitrile/water=70:30 (v/v)

EXAMPLE 1

1-(3-Methylphenyl)pentanol

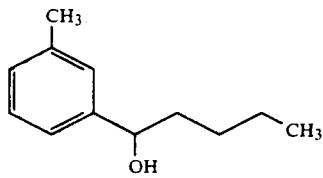

13.4 g of magnesium in 200 ml of absolute ether are initially taken under nitrogen. 75.4 g of n-butyl bromide, dissolved in 300 ml of absolute ether, are added dropwise so that the reaction solution boils.

Thereafter, the mixture is heated under reflux for 1 hour and then cooled to 0° C. 60 g of 3-methylbenzaldehyde, dissolved in 250 ml of absolute ether, are added dropwise at 0° C. The reaction solution is left to stand overnight and is then poured onto 1 l of ice-water. The reaction mixture is acidified with 2N hydrochloric acid. The organic phase is separated off, the aqueous phase is extracted twice with 300 ml of ethyl acetate each time and the combined organic phases are washed twice with 200 ml of water each time, dried over MgSO$_4$ and evaporated on a rotary evaporator in vacuo. The residue is distilled at 64°–66° C./0.02 mm.

Yield: 93% of theory.

The following examples were prepared analogously to Example 1:

EXAMPLE 2

1-(2-Methylphenyl)pentanol

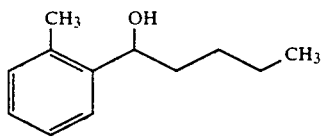

Yield: 84.5% of theory.
Boiling point: 110° C./0.1 mm (bulb tube).

EXAMPLE 3

1-(2-Methylphenyl)heptanol

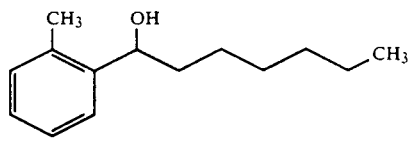

Yield: 95% of theory.
Boiling point: 115° C./0.1 mm (bulb tube).

EXAMPLE 4

1-(3-Methylphenyl)-heptanol

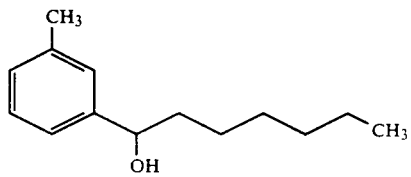

Yield: 91% of theory.
Boiling point: 80°–82° C./0.1 mm.

EXAMPLE 5

1-(2-Methylphenyl)-hexanol

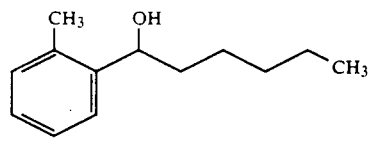

Yield: 94% of theory.
Boiling point: 88° C./0.06 mm.

EXAMPLE 6

1-(3-Methylphenyl)hexanol

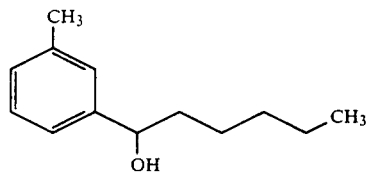

Yield: 88% of theory.
Boiling point: 85°–90° C./0.06 mm.

EXAMPLE 7

1-(4-Methylphenyl)-pentanol

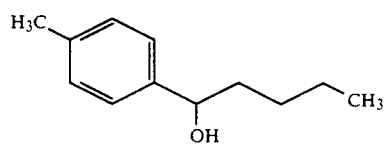

Yield: 71% of theory.
Boiling point: 60°–64° C./0.08 mm.

EXAMPLE 8

3,3-Dimethyl-1-(3-methylphenoxy)-2-butanol

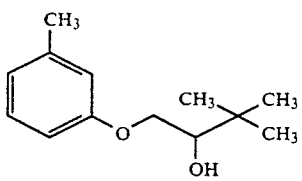

108 g of 3-hydroxytoluene and 101 g of triethylamine are warmed to 120° C. 100.2 g of 3,3-dimethyl-1,2-butene oxide are added dropwise at this temperature in the course of 2.5 hours and the mixture is stirred at 120° C. for 15 hours. After cooling, 500 ml of methylene chloride are added and the mixture is washed 3 times with 500 ml of 2N HCL each time, once with 200 ml of saturated sodium bicarbonate solution and twice with 200 ml of water. The organic phase is dried over $Na_2SO_4$ and concentrated in vacuo and the residue is distilled at 96° C./0.15 mm.

Yield: 76% of theory.

The following compounds were prepared analogously to Example 8:

1-(2-Methylphenoxy)-2-butanol

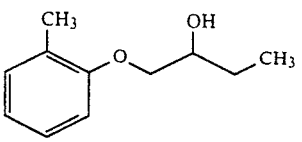

Yield: 93% of theory.
Boiling point: 69°–73° C./0.03 mm.

EXAMPLE 10

1-(3-Methylphenoxy)-2-butanol

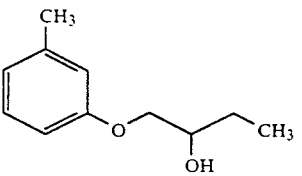

Yield: 91% of theory.
Boiling point: 69°–75° C./0.015 mm.

EXAMPLE 11

2-(3-Methylphenoxy)cyclohexanol (trans form)

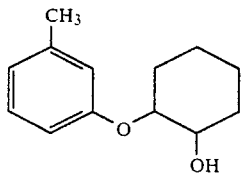

Yield: 47% of theory.
Boiling point: 130°–132° C./0.5 mm.

EXAMPLE 12

1-(3-Methylphenoxy)-2-hexanol

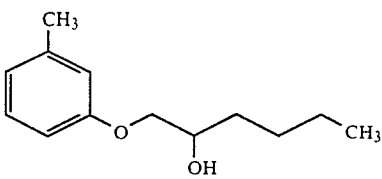

Yield: 59% of theory.
Boiling point: 120°–124° C./0.9 mm.

EXAMPLE 13

1-(3-Methylphenyl)pentyl acetate

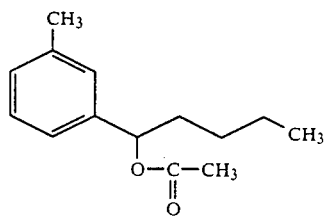

65.4 g of 3-(1-hydroxypentyl)toluene are dissolved in 500 ml of absolute methylene chloride at 0° C., and 104 ml of acetic anhydride, 89 ml of pyridine and 1 g of dimethylaminopyridine are added in succession. The reaction solution is stirred at 0° C. for 1 hour and at 25° C. for 2 hours and then poured onto 1 l of ice-water. After the organic phase has been separated off, it is extracted 3 times with 200 ml of methylene chloride each time. The organic phases are washed 3 times with 200 ml of 2N HCl each time, 3 times with 200 ml of saturated $NaHCO_3$ each time and twice with 200 ml of water each time, dried over magnesium sulphate and concentrated in vacuo. The residue is distilled at 95° C./0.1 mm (bulb tube).

Yield: 95% of theory.
Boiling point: 95° C./0.1 mm (bulb tube).

The following compounds were prepared analogously to Example 13:

EXAMPLE 14

1-(2-Methylphenyl)pentyl acetate

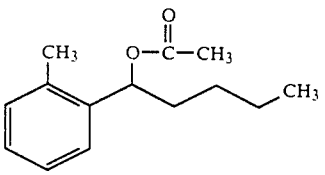

Yield: 93% of theory.
Boiling point: 90° C./0.1 mm (bulb tube).

EXAMPLE 15

1-(2-Methylphenyl)heptyl acetate

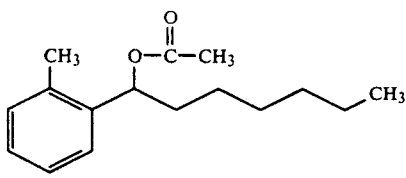

Yield: 94% of theory.
Boiling point: 80°-83° C./0.1 mm.

EXAMPLE 16

1-(3-Methylphenyl)heptyl acetate

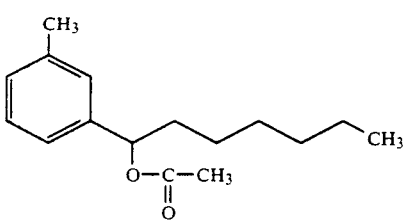

Yield: 96% of theory.
Boiling point: 83°-86° C./0.07 mm.

EXAMPLE 17

1-(2-Methylphenyl)hexyl acetate

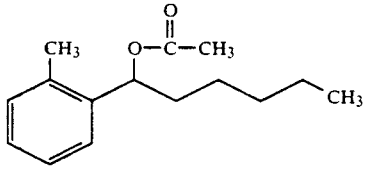

Yield: 87% of theory.
Boiling point: 73°-78° C./0.005 mm.

EXAMPLE 18

1-(3-Methylphenyl)hexyl acetate

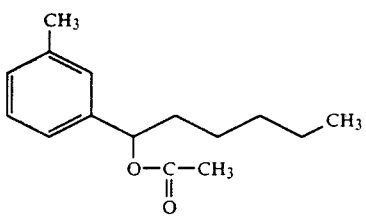

Yield: 86% of theory.
Boiling point: 75°-78° C./0.005 mm.

EXAMPLE 19

1-[(2-Methylphenoxy)methyl]propyl acetate

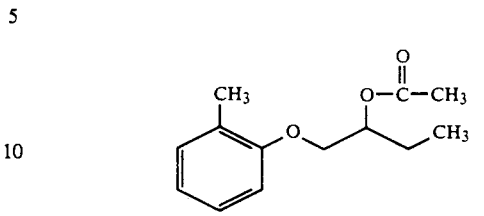

Yield: 85% of theory.
Boiling point: 72°-74° C./0.015 mm.

EXAMPLE 20

1-[(3-Methylphenoxy)methyl]propyl acetate

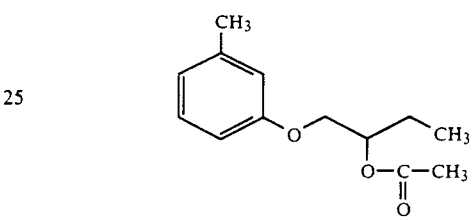

Yield: 90% of theory.
Boiling point: 75°-80° C./0.015 mm.

EXAMPLE 21

2-(3-Methylphenoxy)cyclohexyl acetate (trans form)

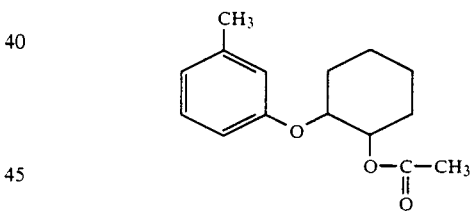

Yield: 86% of theory.
Boiling point: 102°-106° C./0.2 mm.

EXAMPLE 22

2,2-Dimethyl-1-[(3-methylphenoxy)methyl]propyl acetate

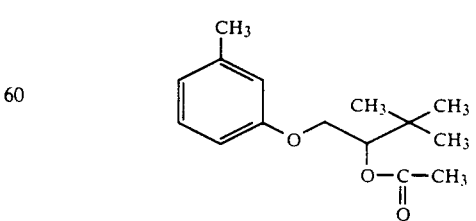

Yield: 91% of theory.
Boiling point: 102° C./0.2 mm.

EXAMPLE 23

1-[(3-Methylphenoxy)methyl]pentyl acetate

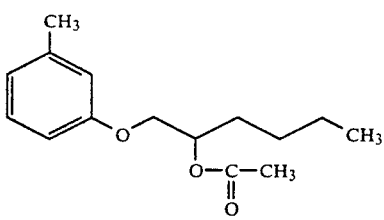

Yield: 89% of theory.
Boiling point: 106°–107° C./0.2 mm.

EXAMPLE 24

1-(4-Methylphenyl)pentyl acetate

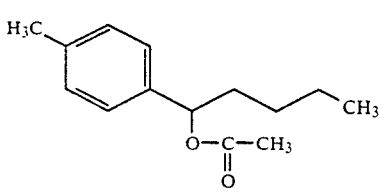

Yield: 83% of theory.
Boiling point: 61°–64° C./0.03 mm.

EXAMPLE 25

1-(3-Bromomethylphenyl)pentyl acetate

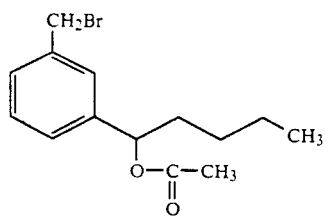

11 g of 3-(1-acetoxy-pentyl)toluene are dissolved in 100 ml of absolute carbon tetrachloride. After addition of 8.9 g of N-bromosuccinimide and 200 mg of azobisisobutyronitrile, the mixture is warmed slowly to the reflux temperature. When the reaction has ended, the mixture is heated under reflux for a further hour and then cooled to 0° C. and the succinimide is filtered off.

After the filtrate has been concentrated in vacuo, the residue is distilled at 97°–102° C./0.08 mm.
Yield: 73% of theory.

The following compounds were prepared analogously to Example 25:

EXAMPLE 26

1(2-Bromomethylphenyl)pentyl acetate

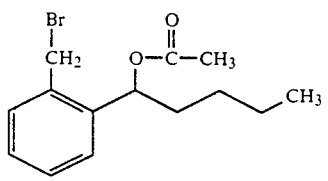

Yield: 72% of theory.
Boiling point: 165° C./0.1 mm (bulb tube).

EXAMPLE 27

1-(2-Bromomethylphenyl)heptyl acetate

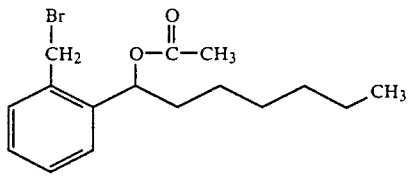

Yield: 83% of theory.
Boiling point: 120° C./0.05 mm.

EXAMPLE 28

1-(3-Bromomethylphenyl)heptyl acetate

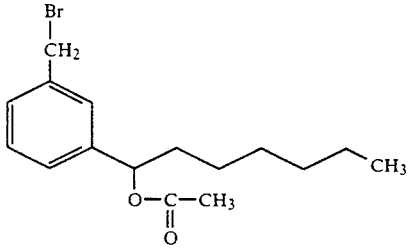

Yield: 75% of theory.
Boiling point: 122° C./0.05 mm.

EXAMPLE 29

1(2-Bromomethylphenyl)hexyl acetate

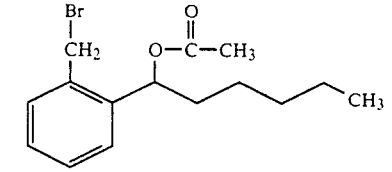

Yield: 75% of theory.
Boiling point: 105° C./0.01 mm.

EXAMPLE 30

1-(3-Bromomethylphenyl)hexyl acetate

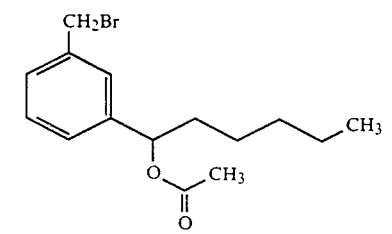

Yield: 84% of theory.
Boiling point: 128° C./0.03 mm.

EXAMPLE 31

1-[(2-Bromomethylphenoxy)methyl]propyl acetate

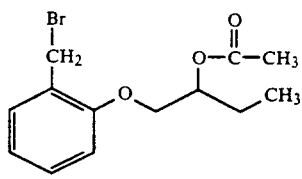

Yield: 82% of theory.
Boiling point: 119°–123° C./0.03 mm.

EXAMPLE 32

1-[(3-Bromomethylphenoxy)methyl)propyl acetate

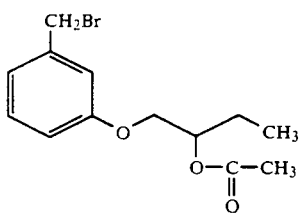

Yield: 70% of theory.
Boiling point: 85°–89° C./0.05 mm.

EXAMPLE 33

2-(3-Bromomethylphenoxy)cyclohexyl acetate (trans form)

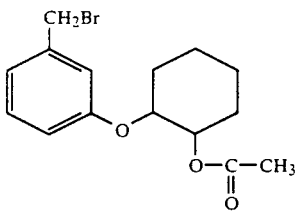

Yield: 65% of theory.
Boiling point: 150°–157° C./0.2 mm.

EXAMPLE 34

1-[(3-Bromomethylphenoxy)methyl]2,2-dimethylpropyl acetate

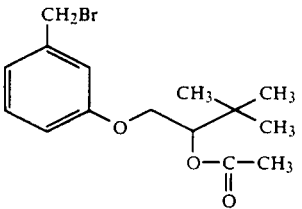

Yield: 58% of theory.
Boiling point: 158°–160° C./0.2 mm.

EXAMPLE 35

1-[(3-Bromomethylphenoxy)methyl]pentyl acetate

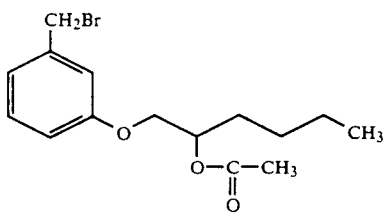

Yield: 57% of theory.
Boiling point: 146°–156° C./0.2 mm.

EXAMPLE 36

1-(4-Bromomethylphenyl)pentyl acetate

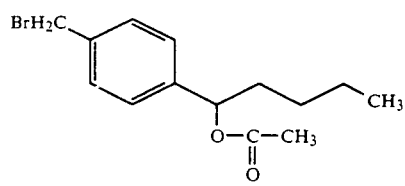

Yield: 46% of theory.
Boiling point: 112° C./0.005 mm.

EXAMPLE 37

1-[3-(Quinolin-8-yloxymethyl)phenyl]pentyl acetate

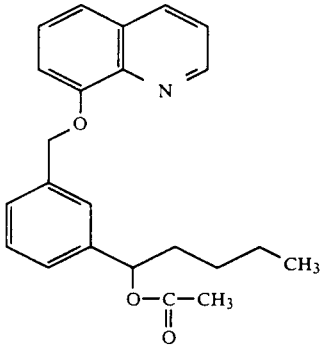

1.45 g of 8-hydroxyquinoline and 1.38 g of ground anhydrous potassium carbonate are stirred in 20 ml of dimethylformamide at 25° C. for 2 hours. 2.99 g of 1-(3-bromomethylphenyl)pentyl acetate, dissolved in 10 ml of dimethylformamide, are then added dropwise and the reaction mixture is stirred overnight. The solvent is distilled off in vacuo, the residue is partitioned between water/ethyl acetate and the organic phase is dried over $Na_2SO_4$ and then concentrated in vacuo. The residue is chromatographed over silica gel 60 (Merck 9385) with $CH_2Cl_2$/methanol 100:5 ($R_f$=0.45). An oil is obtained in a yield of 94% of theory.

The following compounds were prepared analogously to Example 37:

EXAMPLE 38

1-[3-(Quinolin-8-yloxymethyl)phenyl]hexyl acetate

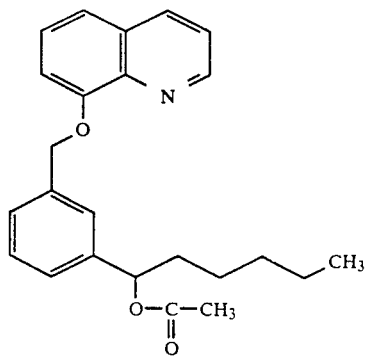

Yield: 68% of theory. R$_f$=3.28 (System b).

EXAMPLE 39

1-[3-(Quinolin-8-yloxymethyl)phenyl]heptyl acetate

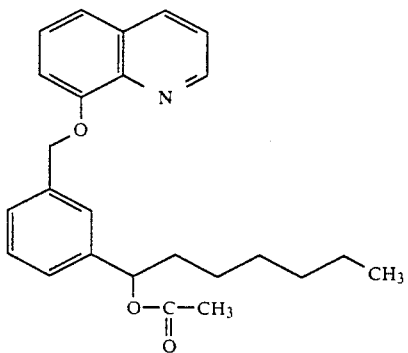

Yield: 62% of theory. R$_f$=3.89 (System b).

EXAMPLE 40

1-[3-(5,7-Dichloroquinolin-8-yloxymethyl)phenyl]heptyl acetate

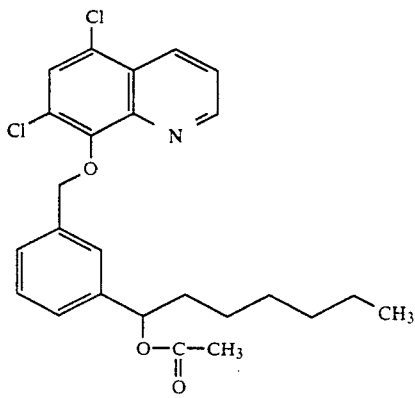

Yield: 69% of theory. R$_f$=7.88 (System a).

EXAMPLE 41

1-[2-(Quinolin-8-yloxymethyl)phenyl]pentyl acetate

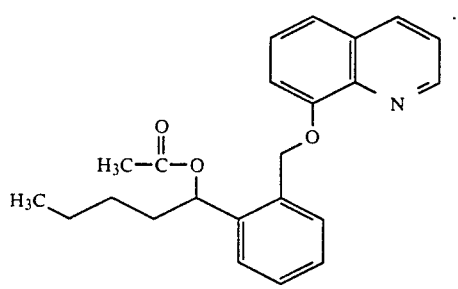

Yield: 83% of theory.

M  g point: 80°–82° C. (cyclohexane). R$_f$=3.29 (System a).

EXAMPLE 42

1-[2-Quinolin-8-yloxymethyl)ph  l]hexyl acetate

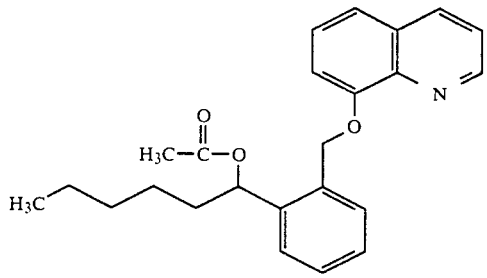

Yield: 66% of theory. R$_f$=3.86 (System a).

Melting point: 79°–81° C. (cyclohexane).

EXAMPLE 43

1-[2-(5,7-Dichloroquinolin-8-yloxymethyl)phenyl]pentyl acetate

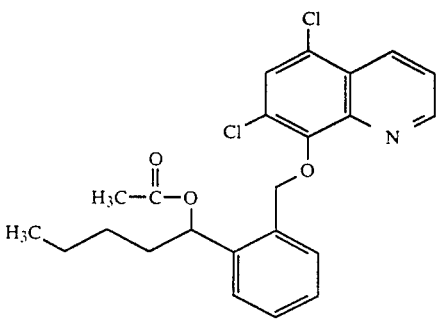

Yield: 77% of theory. R$_f$=6.19 (System a).

EXAMPLE 44

1-[3-(Quinaldin-8-yloxymethyl)phenyl]hexyl acetate

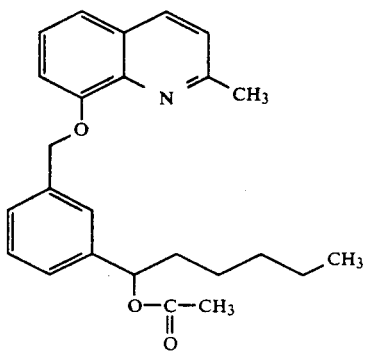

Yield: 67% of theory. R_f=3.71 (System b).

EXAMPLE 45

1-[3-(5,7-Dichloroquinolin-8-yloxymethyl)phenyl]pentyl acetate

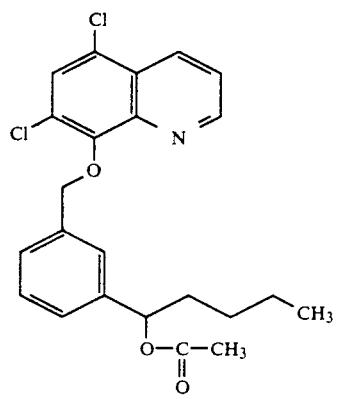

Yield: 50% of theory. R_f=5.52 (System a).

EXAMPLE 46

2-[3-(Quinolin-8-yloxymethyl)phenoxy]cyclohexyl acetate (trans form)

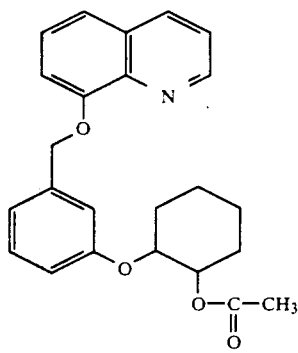

Yield: 77% of theory. R_f+2.47 (System b).
R_f value: 0.25 (cyclohexane/ethyl acetate=2:1).

EXAMPLE 47

1-[3-(Quinolin-8-ylaminomethyl)phenyl]pentyl acetate

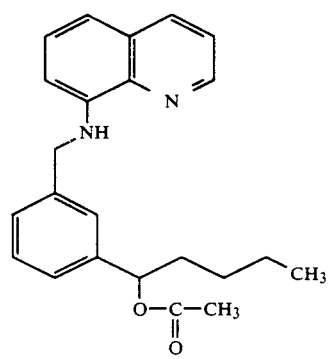

Yield: 63% of theory.

EXAMPLE 48

1-[3-(Isoquinolin-5-yloxymethyl)phenyl]pentyl acetate

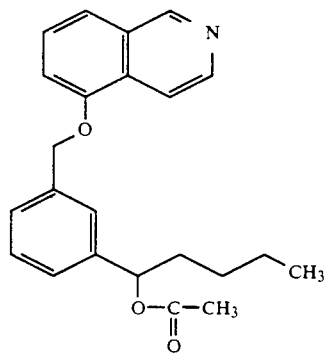

Yield: 46% of theory. R_f=4.08 (System b).
R_f=0.5 (ethyl acetate/cyclohexane=1:1).

EXAMPLE 49

1-[4-(Quinolin-8-yloxymethyl)phenyl]pentyl acetate

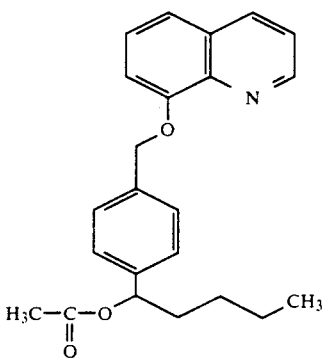

Yield: 75% of theory. R_f=3.06 (System b).

EXAMPLE 50

1-[3-(Quinolin-8-ylthiomethyl)phenyl]-pentyl acetate

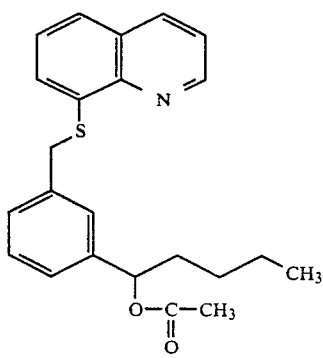

Yield: 95% of theory. R$_f$=3.26 (System b).
R$_f$=0.5 (ethyl acetate/cyclohexane=1:1).

EXAMPLE 51

1-[3-(Quinolin-8-yloxymethyl)phenoxymethyl]-2,2-dimethylpropyl acetate

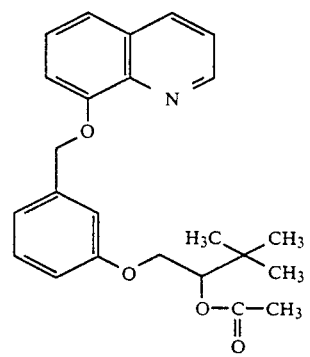

Yield: 93% of theory. R$_f$=2.74 (System b).

EXAMPLE 52

1-[3-(Quinolin-8-yloxymethyl)phenoxymethyl]pentyl acetate

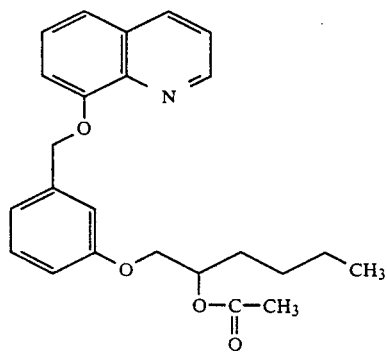

Yield: 70% of theory. R$_f$=2.97 (System b).
Melting point: 85°-86° C. (ethyl acetate/cyclohexane).

EXAMPLE 53

1-[3-(Quinolin-8-yloxymethyl)phenoxymethyl]propyl acetate

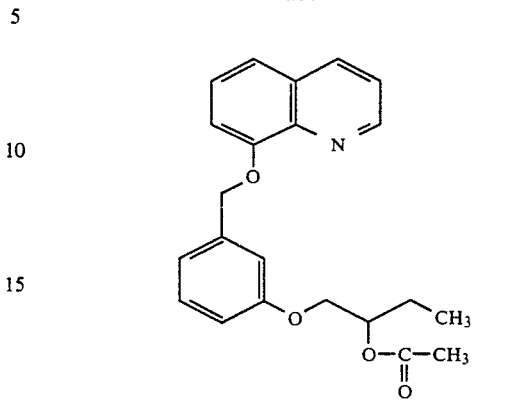

Yield: 61% of theory. R$_f$=2.33 (System b).
Melting point: 77°-79° C. (ethyl acetate/cyclohexane).

EXAMPLE 54

1-[2-(Quinolin-8-yloxymethyl)phenoxymethyl]propyl acetate

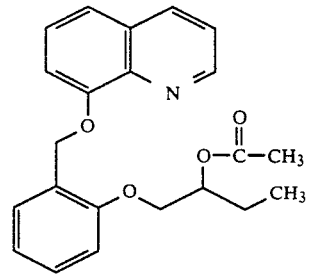

Yield: 84% of theory. R$_f$=2.38 (System b).
R$_f$=0.3 (ethyl acetate/cyclohexane 1:2).

EXAMPLE 55

1-[3-(Quinolin-8-yloxymethyl)phenyl]pentanol

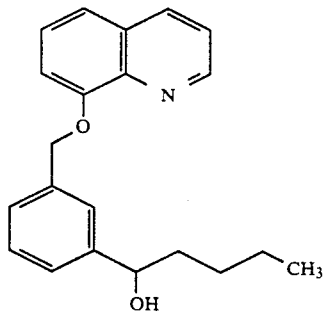

3.63 g of 1-[3-(8-quinoyloxymethyl)phenyl]pentyl acetate are dissolved in 50 ml of methanol. After addition of 10 ml of 2N NaOH, the mixture is stirred at 25° C. for 15 hours, the organic solvent is evaporated in a rotary evaporator in vacuo and the aqueous phase is extracted 3 times with 20 ml of ether each time. The organic phases are washed twice with 30 ml of water each time, dried over Na$_2$SO$_4$ and concentrated in vacuo. The residue is chromatographed over silica gel 60 (Merck 9385) (mobile phase ethyl acetate/cyclohexane 1:2; R$_f$=0.3)

Yield: 91% of theory. R$_f$=2.53 (System a).

Melting Point: 72°–73° C. (diisopropylether).

The following compounds were prepared analogously to Example 55:

EXAMPLE 56

1-[3-(Quinolin-8-yloxymethyl)phenyl]hexanol

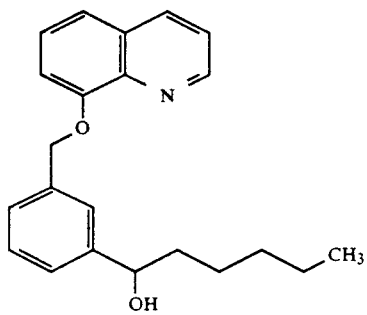

Yield: 78% of theory. R$_f$=2.33 (System b).

EXAMPLE 57

1-[3-(Quinolin-8-yloxymethyl)phenyl]heptanol

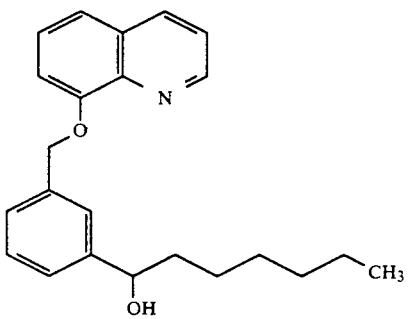

Yield: 77% of theory. R$_f$=2.75 (System b).

EXAMPLE 58

1-[3-(5,7-Dichloroquinolin-8-yloxymethyl)phenyl]heptanol

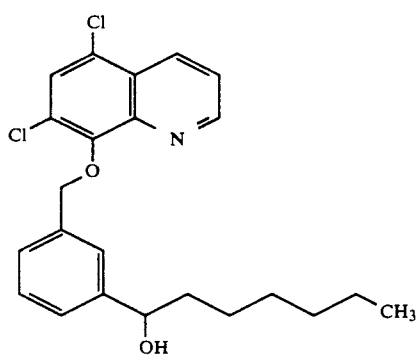

Yield: 86%. R$_f$=5.16 (System a).

EXAMPLE 59

1-[2-(Quinolin-8-yloxymethyl)phenyl]pentanol

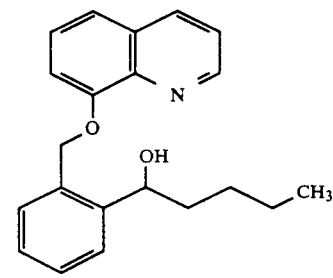

Yield: 80% of theory. R$_f$=2.90 (System a).

EXAMPLE 60

1-[2-(Quinolin-8-yloxymethyl)phenyl]hexanol

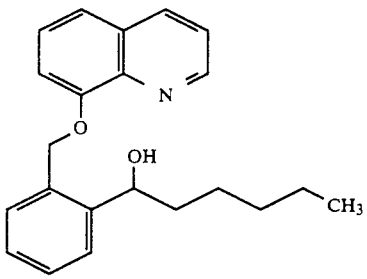

Yield: 81% of theory. R$_f$=2.71 (System b).

EXAMPLE 61

1-[3-(2-methylquinolin-8-yloxymethyl)phenyl]hexanol

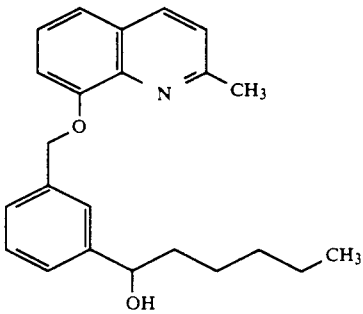

Yield: 86% of therory. R$_f$=2.54 (System b).

EXAMPLE 62

1-[3-(Isoquinolin-5-yloxymethyl)phenyl]pentanol

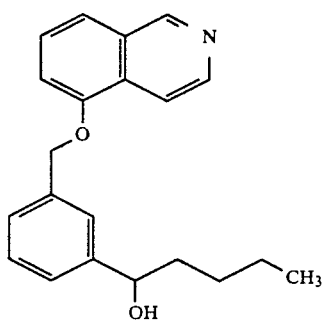

Yield: 16% of theory.
$R_f$=0.3 (CH$_2$CL$_2$:CH$_3$OH=100:2).

EXAMPLE 63

1-[3-(Quinolin-8-ylthiomethyl)phenyl]pentanol

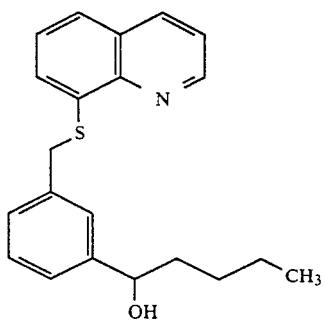

Yield: 63% of theory. $R_f$=2.29 (System b).
$R_f$=0.78 (CH$_2$Cl$_2$: CH$_3$OH=100:5).

EXAMPLE 64

1-[3-(Quinolin-8-ylaminomethyl)phenyl]pentanol

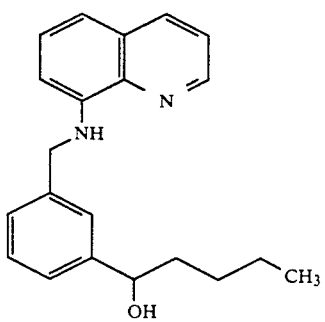

Yield: 51% of theory.

EXAMPLE 65

2-[3-(Quinolin-8-yloxymethyl)phenoxy]cyclohexanol
(trans form)

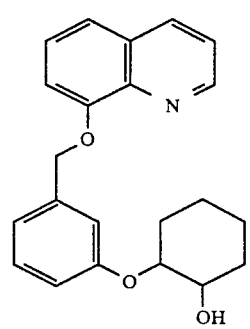

Yield: 65% of theory. $R_f$=1.90 (System b).
Melting point: 109°–110° C. (ethyl acetate/cyclohexane).

EXAMPLE 66

1-[2-(Quinolin-8-yloxymethyl)phenoxymethyl]propanol

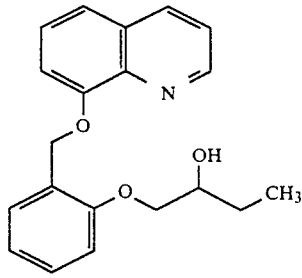

Yield: 83% of theory.
$R_f$: 1.87 (system b).

EXAMPLE 67

1-[3-(Quinolin-8-yloxymethyl)phenoxymethyl]propanol

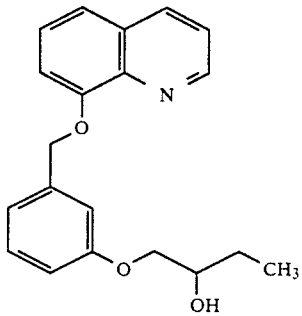

Yield: 98% of theory.
$R_f$=1.75 (system b).

EXAMPLE 68

1-[3-(Quinolin-8-yloxymethyl)phenoxymethyl]pentanol

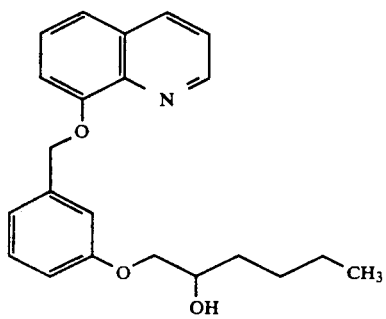

Yield: 98% of theory. $R_f=2.10$ (System b).

EXAMPLE 69

1-[3-(Quinolin-8-yloxymethyl)phenoxymethyl]-2,2-dimethylpropanol

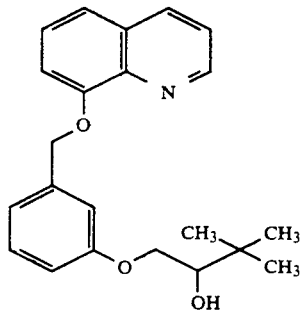

Yield: 95%.
Melting point: 103°–105° C. $R_f=2.07$ (System b).

EXAMPLE 70

1-[2-(Quinoline-N-oxide-8-yloxymethyl)phenyl]hexyl acetate

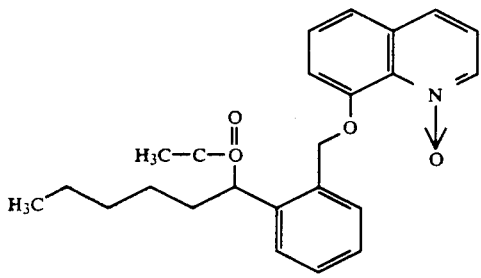

1.4 g of 1[2-(quinolin-8-yloxymethyl)phenyl]hexyl acetate are dissolved in 20 ml of chloroform. 0.64 g of m-chloroperbenzoic acid (80% pure), dissolved in 10 ml of chloroform, are added dropwise at 0° C. in the course of 30 minutes. The mixture is stirred at 25° C. for 15 hours, the solvent is evaporated off and the residue is chromatographed over silica gel 60 (Merck 7734) with ethyl acetate. An oil is obtained.

Yield: 69% of theory. $R_f=2.89$ (System b).

EXAMPLE 71

1-[2-(Quinoline-N-oxide-8-yloxymethyl)phenyl]hexanol

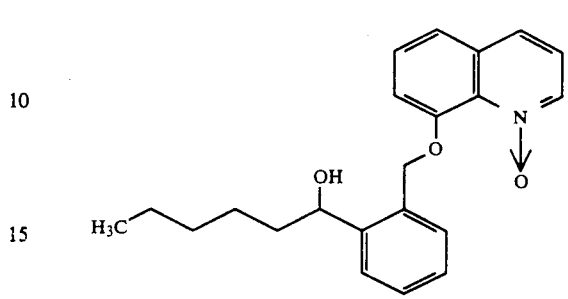

2.2 g of 1-[2-(quinolin-8-yloxymethl)phenyl]hexanol are dissolved in 20 ml of chloroform. 0.64 g of m-chloroperbenzoic acid dissolved in 15 ml of chloroform, are added dropwise at 0° C. in the course of 30 minutes. The mixture is stirred at 25° C. for 15 hours, the solvent is evaporated off and the residue is chromatographed over silica gel 60 (Merck 7734) with methylene chloride/methanol=100:5. The product crystallizes out.

Yield: 26% of theory.
Melting point: 99°–101° C. $R_f=2.89$ (System b).

EXAMPLE 72

1-[2-(2(1H)-quinolon-8-yloxymethyl)phenyl]heptyl acetate

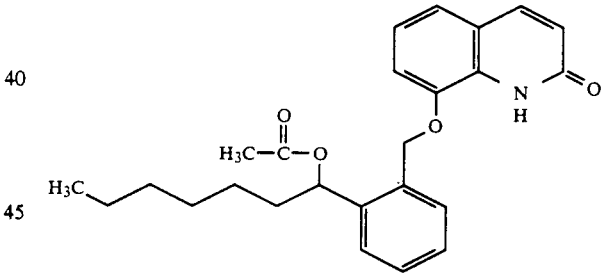

6.5 g of 2,8-dihydroxyquinoline, 5.5 g of anhydrous ground potassium carbonate are stirred in 100 ml of dimethylformamide at 25° C. for 1 hour. After addition of 13.1 g of 1-(2-bromomethylphenyl)heptyl acetate in 50 ml of dimethylformamide, the mixture is stirred at 25° C. for 20 hours. The solvent is removed in vacuo, the residue is taken up in 100 ml of water and the mixture is extracted 3 times with 50 ml of ethyl acetate each time. The organic phases are washed once with 50 ml of water each time, dried over $Na_2SO_4$ and concentrated in vacuo. The oil which remains is chromatographed over silica gel 60 with $CH_2Cl_2$/ethyl acetate 10:1. The resulting product slowly crystallizes out.

Yield: 74% of theory.
Melting point: 113°–115° C. $R_f=3.32$ (System b).

The following compounds were prepared analogously to Example 72:

EXAMPLE 73

1-[2-(2(1H)-Quinolon-8-yloxymethyl)phenyl]hexyl acetate

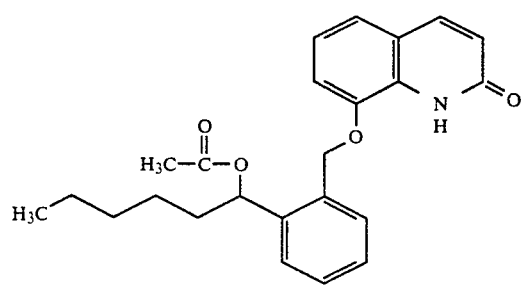

Yield: 43% of theory.

Melting point: 92°–95° C. (cyclohexane). $R_f$=2.86 (system b).

EXAMPLE 74

1-[3-(2(1H)-Quinolon-8-yloxymethyl)phenyl]heptyl acetate

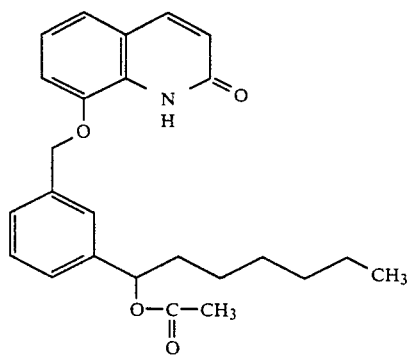

Yield: 50% of theory. $R_f$=3.20 (System b).

EXAMPLE 75

1-[3-(2(1H)-Quinolon-8-yloxymethyl)phenyl]hexyl acetate

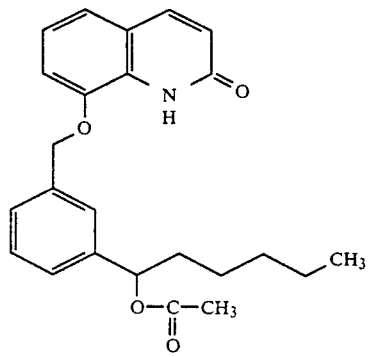

Yield: 48% of theory. $R_f$=2.73 (System b).

EXAMPLE 76

2-[3-(2(1H)-Quinolon-8-yloxymethyl)phenoxy]cyclohexyl acetate (trans form)

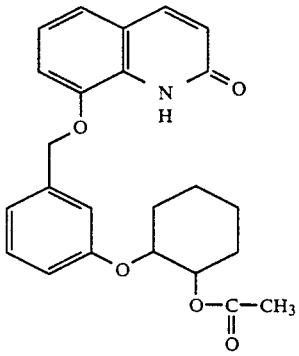

Yield: 67% of theory. $R_f$=2.12 (System b).
$R_f$ value: 0.4 (cyclohexane/ethyl acetate=1:1).

EXAMPLE 77

1-[2-(2(1H)-Quinolon-8-yloxymethyl)phenoxymethyl]-propyl acetate

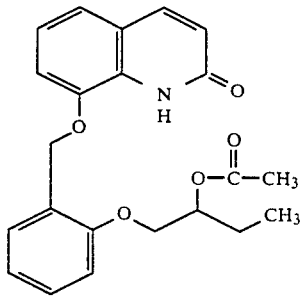

Yield: 48% of theory. $R_f$=2.07 (System b).

Melting point: 112°–114° C. (ethyl acetate/cyclohexane).

EXAMPLE 78

1-[3-(2(1H)-Quinolon-8-yloxymethyl)phenoxymethyl]-propyl acetate

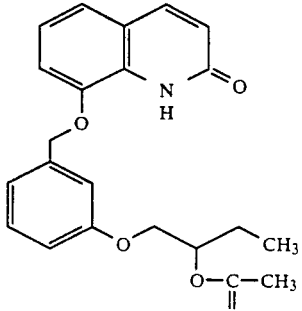

Yield: 65% of theory. $R_f$=2.01 (System b).

Melting point: 81°–84° C. (ethyl acetate/cyclohexane).

EXAMPLE 79

1-[2-(2(1H)-Quinolon-8-yloxymethyl)phenyl]heptanol

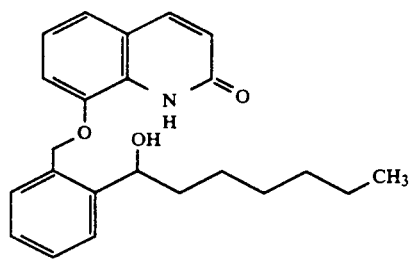

6.0 g of 1-[2-(2(1H)-quinolin-8-yloxymethyl)phenyl]-heptyl acetate are dissolved in 150 ml of methanol, and 60 ml of 1N NaOH are added. The mixture is refluxed for 15 hours. After cooling, 60 ml of 1N HCl are added and the product which has precipitated out is filtered off with suction and recrystallized from isopropanol.

Yield: 50% of theory.

Melting point: 195°-197° C. (isopropanol).

The following compounds were prepared analogously to Example 58:

EXAMPLE 80

1-[2-(2(1H)-Quinolon-8-yloxymethyl)phenyl]hexanol

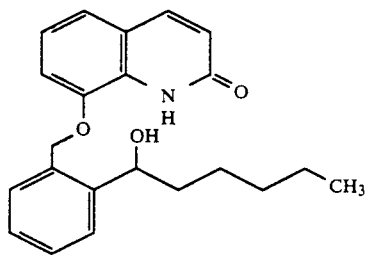

Yield: 74% of theory. $R_f = 2.06$ (System b).
Melting point: 201°-202° C. (isopropanol).

EXAMPLE 81

1-[3-(2(1H)-Quinolon-8-yloxymethyl)phenyl]heptanol

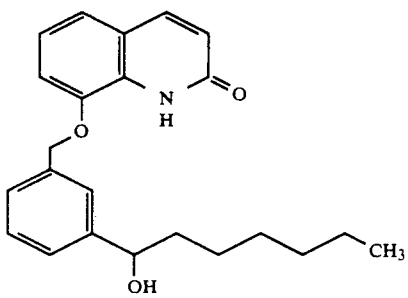

Yield: 85% of theory. $R_f = 2.24$ (System b).
Chromatography on silica gel 60 (Merck 9385) with $CH_2Cl_2:CH_3OH = 100:5$.

EXAMPLE 82

1-[3-(2(1H)-Quinolon-8-yloxymethyl)phenyl]hexanol

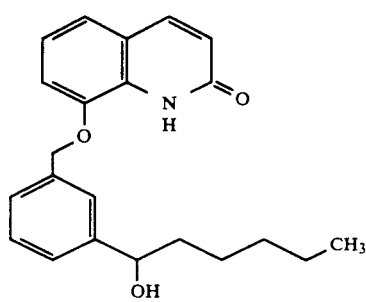

Yield: 90% of theory. $R_f = 1.94$ (System b).
Melting point: 97°-99° C.

EXAMPLE 83

1-[3-(2(1H)-Quinolon-8-yloxymethyl)phenoxymethyl]-propanol

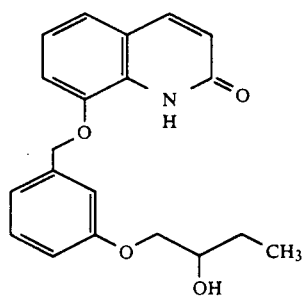

Yield: 54% of theory. $R_f = 1.56$ (System b).
$R_f = 0.43$ $(CH_2Cl_2/CH_3OH = 100:5)$.

EXAMPLE 84

2-[3-(2(1H)-Quinolon-8-yloxymethyl)phenoxy]cyclohexanol (trans form)

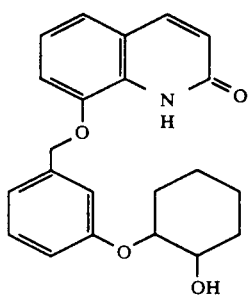

Yield: 89% of theory. $R_f = 1.62$ (System b).
$R_f = 0.5$ $(CH_2Cl_2/CH_3OH = 100:4)$.

EXAMPLE 85

1-[2-(2(1H)-Quinolon-8-yloxymethyl)phenoxymethyl]-propanol

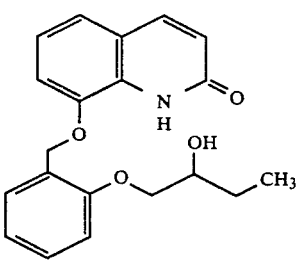

Yield: 89% of theory.
Melting point: 114°–116° C.
$R_f$=1.66 (System b).

The following were prepared analogously to Example 1:

EXAMPLE 86

3-methyl-1-(3-methylphenyl)butanol

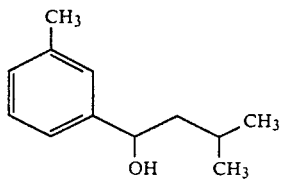

Yield: 35% of theory.
Boiling point: 72°–76° C./0.008 mm.

The following were prepared analogously to Example 23:

EXAMPLE 87

[3-methyl-1-(3-methylphenyl)]butyl acetate

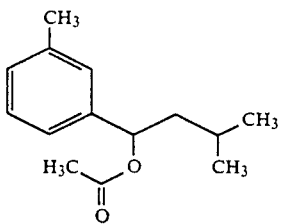

Yield 71% of theory.
Boiling point: 54°–56° C./0.005 mm.

EXAMPLE 88

1-(3-methylphenyl)hexyl propionate

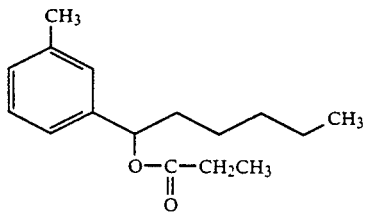

Yield: 75% of theory.
Boiling point: 78°–80° C./0.005 mm.

The following were prepared analogously to Example 25:

EXAMPLE 89

[1-(3-bromomethylphenyl)-3-methyl]butyl acetate

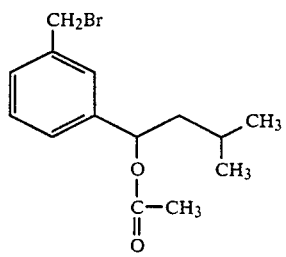

Yield: 52%.
Boiling point: 93° C./0.025 mm.

EXAMPLE 90

[1-(3-bromomethylphenyl)]hexyl propionate

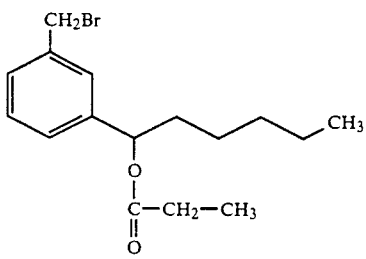

Yield: 56% of theory.
Boiling point: 111° C./0.02 mm.

The following were prepared analogously to Example 37:

EXAMPLE 91

1-[3-(quinolin-8-yloxymethyl)phenyl]-3-methylbutyl acetate

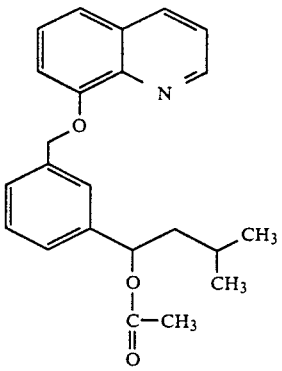

Yield: 88% of theory.
$R_f$=3.31 (System b).

EXAMPLE 92

1-[3-(quinolin-8-yloxymethyl)phenyl]hexyl propionate

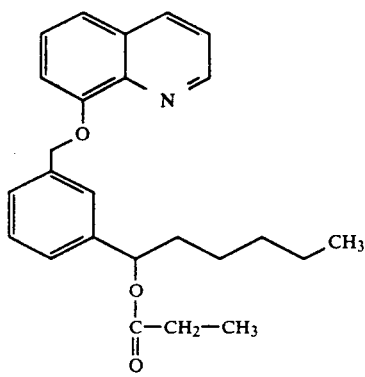

Yield: 83% of theory.
R_f=4.11 (System b).

EXAMPLE 93

1-[3-(4-methylquinolin-8-yloxymethyl)-phenyl]-pentyl acetate

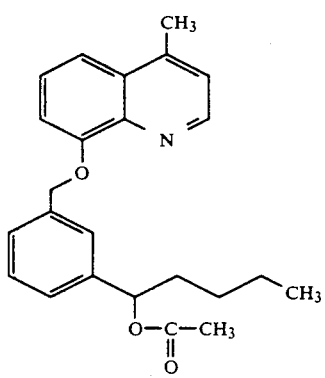

Yield: 59% of theory.
Melting point: 67°-70° C.
R_f=2.95 (System b).

EXAMPLE 94

1-[3-(4-chloroquinolin-8-yloxymethyl)phenyl]-pentyl acetate

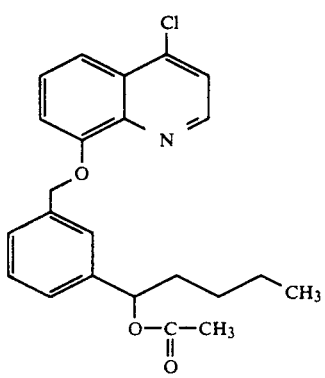

Yield: 60% of theory.
R_f=3.60 (System b).

EXAMPLE 95

1-[3-(6-methylquinolin-8-yloxymethyl)-phenyl]-pentyl

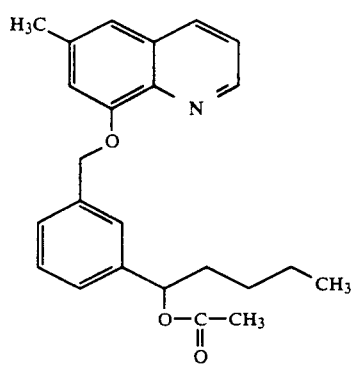

Yield: 51% of theory.
R_f=3.29 (System b).

EXAMPLE 96

1-[3-(6-nitroquinolin-8-yloxymethyl)phenyl]-pentyl acetate

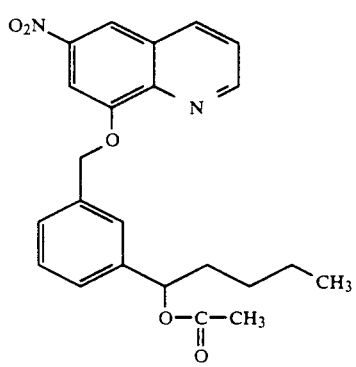

Yield: 45% of theory.
Melting point: 72°-74° C. (Isopropanol).
R_f=2.74 (System b).

EXAMPLE 97

1-[3-(2-ethylsulphonylbenzothiazol-7-yl-aminomethyl)-phenyl]hexyl acetate

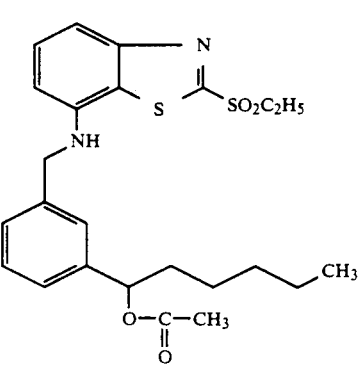

Yield: 34% of theory.
The following were prepared analogously to Example 55:

EXAMPLE 98

1-[4-(quinolin-8-yloxymethyl)phenyl]pentanol

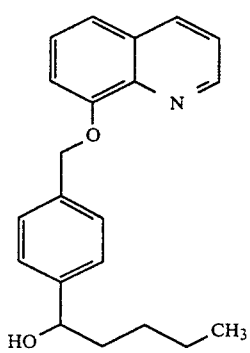

Yield: 86% of theory.
R$_f$=2.04 (System b).

EXAMPLE 99

1-[3-(quinolin-8-yloxymethyl)phenyl]-3-methyl-butanol

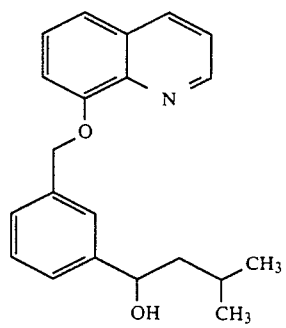

Yield: 68% of theory.
R$_f$=2.12 (System b).

EXAMPLE 100

1-[3-(2-methylbenzothiazol-7-yloxymethyl)phenyl]pentanol

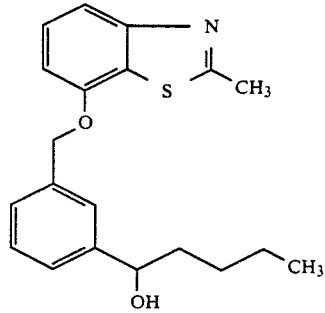

Yield: 61% of theory.
R$_f$=2.31 (System b).

EXAMPLE 101

1-[3-(2-ethylsulphonylbenzothiazol-7-yloxymethyl)-phenyl]hexanol

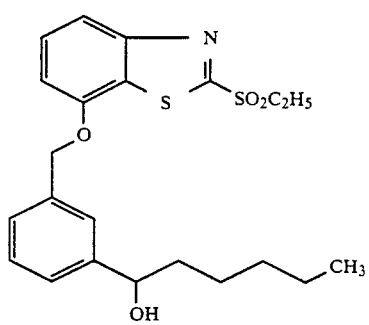

Yield: 30% of theory.
R$_f$=2.95 (System b).

EXAMPLE 102

1-[3-(4-chloroquinolin-8-yloxymethyl)phenyl]pentanol

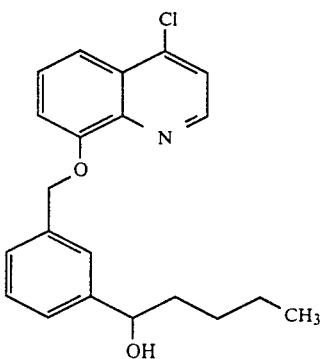

Yield: 91% of theory.
R$_f$=2.35 (System b).

EXAMPLE 103

1-[3-(4-methylquinolin-8-yloxymethyl)phenyl]pentanol

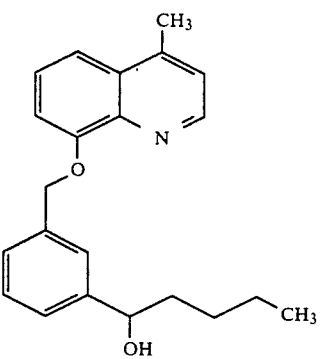

Yield: 74% of theory.
Melting point: 94°–96° C.
R$_f$=2.21 (System b).

EXAMPLE 104

1-[3-(6-methylquinolin-8-yloxymethyl)phenyl]pentanol

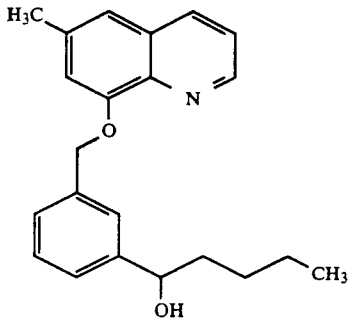

Yield: 96% of theory.

$R_f = 2.22$ (System b).

EXAMPLE 105

8-[3-(1-methoxypentyl)benzyl]oxyquinoline

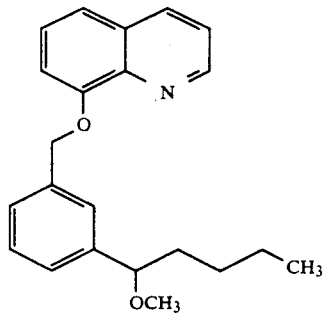

A solution of 1.6 g (5.0 mmol) of 1-[3-(quinolin-8-yloxymethyl)phenyl]pentanol in 20 ml of tetrahydrofuran is added dropwise to a suspension of 0.13 g (5.5. mmol) of sodium hydride in 10 ml of tetrahydrofuran under a protective gas in the course of 30 minutes at 25° C. Thereafter, 0.35 ml of methyl iodide is added dropwise and the mixture is stirred for 15 hours at 25° C. After the addition of 5 ml of methanol, the mixture is evaporated down, the residue is taken up in ether, and the solution is washed with water, dried over sodium sulphate and evaporated down again. The residue is chromatographed over silica gel 60.

(Mobile phase 100:2 dichloromethane/methanol).

Yield: 54% of theory.

$R_f = 3.48$ (System a).

EXAMPLE 106

1-[3-(quinolin-8-yloxymethyl)phenyl]pentyl benzoate

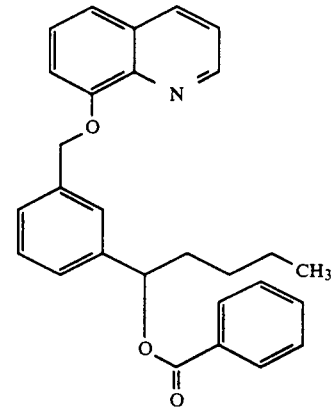

3.2 g (10 mmol) of 1-[3-(quinolin-8-yloxymethyl)phenyl]-pentanol are dissolved in 50 ml of dichloromethane. After the addition of 2.8 ml of triethylamine and 1.16 ml of benzoyl chloride, the mixture is stirred for 2 hours at 25° C. and then heated under reflux for 5 hours. The reaction mixture is washed three times with water, dried over sodium sulphate and evaporated down. The residue is chromatographed over silica gel 60 (mobile phase: 100:2 dichloromethane/methanol). An oil is obtained.

Yield: 45% of theory.

$R_f = 4.22$ (System b).

Use Example:

EXAMPLE 107

The pharmacological action of the substances according to the invention was determined by the following method:

The release of leukotriene B4 (LTB4) was determined on polymorphonuclear rat leucocytes (PMN) by means of reverse phase high performance liquid chromatography, after addition of substances and Ca ionophor, in accordance with the method of Borgeat, P. et al., Proc. Nat. Acad. Sci., 76, 2148–2152 (1979) as a measure of the lipoxygenase inhibition. The in vivo activity of the compounds was demonstrated with the mouse ear inflammation model in accordance with the method of Young, J. M. et al., J. of Investigative Dermatology, 82, 367–371 (1984).

The values determined by these tests for some compounds according to the invention are listed by way of example in Table 1:

| Example | LO inhibition IC$_{50}$ values (g/ml) | Inhibition of inflammation at 2 mg/ear (%) |
| --- | --- | --- |
| 38 | $1.4 \times 10^{-7}$ | 75.0 |
| 39 | $2.6 \times 10^{-7}$ | 72.0 |
| 55 | $8.3 \times 10^{-8}$ | 70.0 |
| 57 | $2.3 \times 10^{-7}$ | 86.1 |

We claim:

1. A substituted benzyl ether, benzyl thioether or benzylamine of the formula

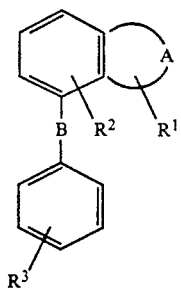

in which
R¹ and R² each independently represent hydrogen, C₁-C₁₂-alkyl, C₂-C₁₂-alkenyl, C₅-C₈-cycloalkyl, C₁-C₁₂-alkoxy, C₁-C₁₂-alkylthio, C₁-C₆-halogenoalkyl, C₁-C₆-halogenoalkoxy, C₁-C₆-halogenoalkylthio, C₁-C₁₂-sulphonylalkyl, C₇-C₁₄-aralkoxy, C₇-C₁₄-aralkylthio, halogen, nitro, cyano or hydroxyl, or represent a group of the formula

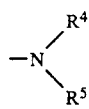

wherein
R⁴ and R⁵ each independently represent hydrogen, C₁-C₁₂-alkyl, C₂-C₁₂-alkenyl, C₅-C₈-cycloalkyl, phenyl, naphthyl, bisphenyl, benzyl, naphthylmethyl, phenethyl, phenylpropyl or C₁-C₆-acyl,
R³ represents a group of the formula

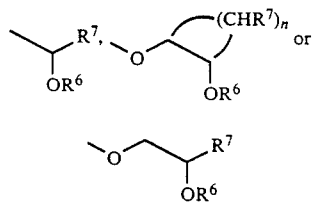

in which
R⁶ represents hydrogen, C₁-C₁₂-alkyl or C₁-C₆-acyl,
R⁷ represents hydrogen or C₁-C₁₂-alkyl and
n represents a number from 3 to 10,
B represents —CH₂—X— or —X—CH₂,
wherein
X represents O, S or NR⁷,
and wherein
R⁷ has the abovementioned meaning and the group

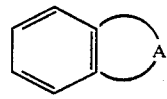

represents quinoline, 2-quinolone or quinoline-N-oxide.

2. A substituted benzyl ether, benzyl thioether or benzylamine according to claim 1,
wherein
R¹ and R² each independently represent hydrogen, C₁-C₈-alkyl, C₂-C₆-alkenyl, cyclopentyl, cyclohexyl, C₁-C₆-alkoxy, C₁-C₆-alkylthio, C₁-C₄-halogeno alkyl, C₁-C₆-halogeno alkoxy, C₁-C₄-halogeno alkylthio, C₁-C₄-sulphonyl alkyl, benzyloxy, benzylthio, fluorine, chlorine, bromine, nitro, cyano or hydroxyl, or represent a group of the formula

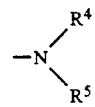

wherein
R⁴ and R⁵ are identical or different and represent hydrogen, C₁-C₈-alkyl, C₂-C₆-alkenyl, cyclopentyl, cyclohexyl, benzyl, phenyl, benzoyl, or acetyl,
R³ represents a group of the formula

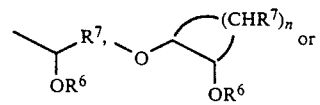

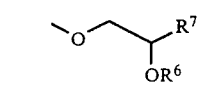

wherein
R⁶ represents hydrogen, C₁-C₈-alkyl, benzoyl or C₁-C₄-alkanoyl,
R⁷ represents hydrogen or C₁-C₈-alkyl and n represents a number from 3 to 8,
B represents —CH₂—X—,
and wherein
X represents O, S or NR⁷.

3. A substituted benzyl ether, benzylthioether or benzylamine according to claim 1,
wherein
R¹ and R² each independently represent hydrogen, methyl, ethyl, propyl, isopropyl, allyl, methoxy, ethoxy, methylthio, ethylthio, trifluoromethoxy, trifluoromethylthio, fluorine, chlorine, bromine, nitro, cyano, ethyl sulphonyl, or hydroxyl, or represent a group of the formula

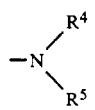

wherein
R⁴ and R⁵ each independently represent hydrogen, methyl, ethyl, propyl, isopropyl, allyl, benzyl, phenyl or acetyl,
R³ represents a radical of the formula

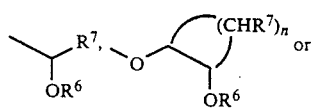

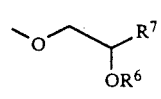

wherein $R^6$ represents hydrogen, methoxy, benzoyl, acetyl, ethylcarbonyl or propylcarbonyl, $R^7$ represents hydrogen, or represents 3 to 8 straight or branched alkyl chain with 3 to 8 C atoms and n represents a number from 3 to 4, B represents —$CH_2$—X—, and wherein X represents O, S or $NR^7$.

4. A pharmaceutical composition useful in the inhibition of lipoxygenase comprising an amount effective to inhibit lipoxygenase of a substituted benzyl ether, benzylthioether or benzylamine according to claim 1 and a pharmaceutically acceptable excipient or solvent.

5. A pharmaceutical composition useful in the inhibition of lipoxygenase comprising an amount effective to inhibit lipoxygenase of a substituted benzyl ether, benzylthioether or benzylamine according to claim 2 and a pharmaceutically acceptable excipient or solvent.

6. A pharmaceutical composition useful in the inhibition of lipoxygenase comprising an amount effective to inhibit lipoxygenase of a substituted benzyl ether, benzylthioether or benzylamine according to claim 3 and a pharmaceutically acceptable excipient or solvent.

* * * * *